United States Patent
Uematsu

(10) Patent No.: US 7,603,164 B2
(45) Date of Patent: Oct. 13, 2009

(54) COMPOSITE SYSTEM FOR RADIATION THERAPY

(75) Inventor: Minoru Uematsu, 651 Yamanouchi, Kamakura-shi, Kanagawa-ken (JP)

(73) Assignees: Minoru Uematsu, Kamakura-shi (JP); Masayuki Atsuchi, Kagoshima-shi (JP); James Robert Wong, Morristown, NJ (US)

( * ) Notice: Subject to any disclaimer, the term of this patent is extended or adjusted under 35 U.S.C. 154(b) by 694 days.

(21) Appl. No.: 10/614,510

(22) Filed: Jul. 8, 2003

(65) Prior Publication Data

US 2004/0034438 A1    Feb. 19, 2004

(30) Foreign Application Priority Data

Aug. 14, 2002  (JP) .............................. 2002-236282
Feb. 6, 2003  (JP) .............................. 2003-029272

(51) Int. Cl.
  *A61B 5/05*    (2006.01)
(52) U.S. Cl. ................. 600/427; 378/63; 5/601
(58) Field of Classification Search ................ 600/427, 600/425, 411, 415; 378/21, 65, 68, 20, 63; 5/600, 601
  See application file for complete search history.

(56) References Cited

U.S. PATENT DOCUMENTS 5,039,867 A * 8/1991 Nishihara et al. ........ 250/492.3

(Continued)

FOREIGN PATENT DOCUMENTS

DE  199 08 494 A  10/2000

(Continued)

OTHER PUBLICATIONS

Liu, et al., "Cone-beam reconstruction for a c-arm CT system", Nov. 2001, IEEE, pp. 1489-1493.*

(Continued)

*Primary Examiner*—Long V Le
*Assistant Examiner*—Jacqueline Cheng
(74) *Attorney, Agent, or Firm*—Birch, Stewart, Kolasch & Birch, LLP

(57) ABSTRACT

A composite system for radiation therapy includes a CT scanner for checking the position of an affected portion of a patient to be irradiated, an irradiation apparatus for disposing, on the basis of positional information of the affected portion checked by the CT scanner, the patient at a specific position at which the affected portion is aligned to an irradiation position, and performing irradiation to the affected portion, a common bed used for the CT scanner and the irradiation apparatus, in a state that the patient lies on the common bed and moving means for moving the patient from the CT scanner to the specific position of the irradiation apparatus. The moving means moves the patient on the common bed to the specific position by causing either of linear movement of the CT scanner and the irradiation apparatus, linear movement of the CT scanner and curved movement of the irradiation apparatus, curved movement of the CT scanner and the irradiation apparatus and linear movement of the CT scanner, linear movement of the CT scanner and the common bed, and linear movement of the CT scanner and curved movement of the common bed. With this composite system, at the time of radiation therapy for tumor or the like, the affected portion can be irradiated in a state that the position of the affected portion aligned by a CT scanner is accurately kept. As a result, it is possible to significantly enhance the control of the positional accuracy of the affected portion in radiation therapy and hence to significantly increase the effect of the radiation therapy.

7 Claims, 15 Drawing Sheets

U.S. PATENT DOCUMENTS

| | | | | |
|---|---|---|---|---|
| 5,259,011 A | * | 11/1993 | Petro | 378/4 |
| 5,525,905 A | * | 6/1996 | Mohapatra et al. | 324/318 |
| 5,537,452 A | * | 7/1996 | Shepherd et al. | 378/65 |
| 5,615,430 A | * | 4/1997 | Nambu et al. | 5/600 |
| 5,851,182 A | | 12/1998 | Sahadevan | |
| 6,094,760 A | * | 8/2000 | Nonaka et al. | 5/601 |
| 6,195,578 B1 | * | 2/2001 | Distler et al. | 600/415 |
| 6,205,347 B1 | * | 3/2001 | Morgan et al. | 600/407 |
| 6,269,143 B1 | | 7/2001 | Tachibana | |
| 6,302,579 B1 | * | 10/2001 | Meyer et al. | 378/196 |
| 6,377,830 B1 | * | 4/2002 | Carrozzi et al. | 600/407 |
| 6,385,480 B1 | * | 5/2002 | Bachus et al. | 600/411 |
| 6,508,586 B2 | * | 1/2003 | Oota | 378/196 |
| 6,640,364 B1 | * | 11/2003 | Josephson et al. | 5/601 |
| 6,845,258 B2 | * | 1/2005 | Bartels et al. | 600/407 |
| 6,928,142 B2 | * | 8/2005 | Shao et al. | 378/63 |
| 6,961,606 B2 | * | 11/2005 | DeSilets et al. | 600/415 |
| 6,984,827 B2 | * | 1/2006 | Tomura et al. | 250/394 |
| 7,382,851 B2 | * | 6/2008 | Inoue et al. | 378/4 |
| 2001/0007588 A1 | | 7/2001 | Iizuka | |
| 2002/0039403 A1 | * | 4/2002 | Oota | 378/196 |
| 2004/0030246 A1 | * | 2/2004 | Townsend et al. | 600/427 |
| 2004/0210126 A1 | * | 10/2004 | Hajaj et al. | 600/407 |

FOREIGN PATENT DOCUMENTS

| | | |
|---|---|---|
| EP | 0 562 585 A | 9/1993 |
| JP | 01 052436 A | 2/1989 |
| JP | 09 192245 A | 7/1997 |
| JP | 9-192245 A | 7/1997 |
| JP | 10-127793 | 5/1998 |
| JP | 11-009708 | 1/1999 |
| JP | 2000 288102 A | 2/2001 |
| JP | 2001-137221 | 5/2001 |
| JP | 2001-190535 | 7/2001 |
| JP | 2002-006044 | 1/2002 |
| JP | 2002-288102 | 10/2002 |
| JP | 2003-190149 | 7/2003 |
| JP | 2004049819 A * | 2/2004 |
| JP | 2005-052306 | 3/2005 |

OTHER PUBLICATIONS

Uematsu, Minoru et al; American Cancer Society, vol. 82, No. 6, pp. 1062-1070, (1998).

Uematsu, Minoru et al; Int. J. Radiation Oncology Biol.Phys., vol. 35, No. 3, pp. 587-592, (1996).

Uematsu, Minoru et al; Int. J. Radiation Oncology Biol. Phys., vol. 51, No. 3, pp. 666-670, (2001).

European Office Action (issued Jul. 15, 2004) submitted in Information Disclosure Statement of Jan. 25, 2005.

* cited by examiner

COMPOSITE SYSTEM FOR RADIATION THERAPY

BACKGROUND OF THE INVENTION

1. Field of the Invention

The present invention relates to a composite system for radiation therapy (equipment for radiation therapy) capable of carrying out a series of radiation therapy operations for tumor or the like, specifically, an operation of accurately performing alignment of an affected portion (equivalent to target area) to be irradiated of a patient by a CT scanner, an operation of moving the patient to an irradiation apparatus such that the affected portion is matched to an irradiation position of the irradiation apparatus (equivalent to radiation therapy apparatus), and an operation of performing irradiation to the affected portion.

In particular, the present invention relates to a composite system for radiation therapy, which includes a common bed that is used for a CT (Computer tomography) scanner and an irradiation apparatus, and also X-ray simulator (optionally used), in state that the patient lies on the common bed, at the time of moving a patient to an irradiation apparatus (e.g. linear accelerator, proton machine) such that an affected portion of the patient is matched to an irradiation position of the radiation therapy, and means for moving the patient on the common bed to a specific position of each of the CT scanner and the irradiation apparatus, and also X-ray simulator (optionally used), without any rotational movement of the common bed, thereby suppressing occurrence of a positional error caused between alignment of an affected portion and irradiation thereof, and greatly improving the control of accuracy in therapy position at the time of radiation therapy.

The present invention further relates to a composite system for radiation therapy including the common bed having an isocentric rotation function or an isocentric rotation mechanism allowing the common bed to be rotated around an isocenter position (equivalent to an irradiation center upon irradiation of a target site of a patient to irradiated at different angles), thereby allowing the effective use of the isocentric rotation mechanism not only at the time of radiation therapy but also at the time of inspection by a CT scanner, an X-ray simulator (optionally used), and the like.

2. Description of the Related Art

In radiation therapy for tumor or the like of a patient, it may be desirable to search the position of the tumor (target area) by a CT scanner in a state that the patient lies on a bed, and to irradiate, in such a correct alignment state, to the affected portion (target area). In related art equipment for radiation therapy, however, only a therapy apparatus like as a linear accelerator (irradiation apparatus) or the like is installed in a radiation therapy room, and a CT scanner for alignment is generally installed in a room separated from the radiation therapy room. Accordingly, a patient, whose affected portion has been accurately imaged or aligned by a CT scanner in a room separated from a radiation therapy room, must be moved to the radiation therapy room for irradiation by the irradiation apparatus, and therefore, the patient cannot be directly subjected to irradiation with the aligned position by the CT scanner accurately kept as it is.

The present inventor has found that the movement of a patient from a CT scanner present in a room separated from a radiation therapy room to an irradiation apparatus present in the radiation therapy room brings a positional error being as large as not negligible, and to eliminate such a positional error, the present inventor has developed an integral type composite system for radiation therapy (radiation therapy system) configured by disposing both a linear accelerator (irradiation apparatus) and an X-ray CT scanner or diagnostic type CT scanner in the same room and connecting them by means of a common bed (Japanese Laid-Open Patent Publication No. Hei-9/192245). Since that time, favorable results have been reported on radiation therapy for various kinds of tumors by using such a new integral type composite system for radiation therapy (Cancer Mar. 15, 1998/Volume 82/Number 6, p. 1062-1070).

In the above-described integral type composite system for radiation therapy, to accurately perform alignment of an affected portion of a patient by a CT scanner and match the aligned position of the affected portion to an irradiation position of a linear accelerator (irradiation apparatus), the movement of the patient from the CT scanner to the irradiation apparatus has been performed as shown in FIG. 14. The integral type composite system for radiation therapy, denoted by character A13 in the figure, includes a CT scanner 1, an irradiation apparatus 2, and a rotary bed 30, wherein a patient on the rotary bed 30 is moved between the CT scanner 1 and the irradiation apparatus 2 by rotational movement of the rotary bed 30 by an angle of 180° along a circular direction (shown by an arrow "g") around a rotational center "r'" (the prop of the rotary type bed 30).

In the case of moving a patient by rotational movement of the rotary bed 30, however, it is required for the operator(s) to carefully handle the rotary bed so as not to cause any positional error(s). From this viewpoint, the movement of a patient by using the rotary bed has a room to be improved. The integral type composite system for radiation therapy using the rotary bed has another disadvantage that in order to check whether or not a coordinate of the CT scanner and a coordinate of the irradiation apparatus are joined to each other via the rotational movement by the rotary bed, it is required to turn the rotary bed again by an angle of 180° so as to be matched again to the CT scanner, followed by re-radiograph or re-imaging. Even in the viewpoint of control of positional accuracy, the movement of a patient by using the rotary bed has a room to be improved.

In recent years, a therapy bed having an isocentric rotation function allowing the bed to be rotated around an isocenter (irradiation center) has been used for radiation therapy. As shown in FIG. 15, an isocentric rotation mechanism D having such an isocentric rotation function is configured as follows. A turn table 20b is installed on a floor face 5 at a position near an irradiation apparatus in such a manner that the upper surface of the turn table 20b is nearly at the same level (plane) as the upper plane of the floor face 5. An end portion of a rotational disk 20d is integrally mounted to the turn table 20b. A base 20c of a therapy bed 20 is mounted on the rotational disk 20d in such a manner that the therapy bed 20 is isocentrically rotatable around an axial center "r" of the turn table 20b. However, the use of such a function for an inspection apparatus for confirming and aligning the position of a lesion, for example, a CT scanner has been not examined. Even the above-described rotary bed 30 has an isocentric rotation mechanism upon use for an irradiation apparatus by means of a turn table installed on a floor face at a position on the irradiation apparatus side; however, the rotary bed 30 cannot make use of the isocentric rotation mechanism upon use for a CT scanner because the bed 30 is rotated around the center "r'".

By the way, in a radiation therapy system in which the position of an affected portion is checked by a CT scanner and the affected portion is matched to an irradiation position of an irradiation apparatus, the alignment of the affected portion is mainly determined by the CT scanner used, and to most accurately perform the alignment of the affected portion by the CT scanner, it may be desirable to locate, at the time of scanning of the affected portion (lesion) by the CT scanner, the center of the affected portion at the center of a detectable region (a tunnel portion of a gantry) of the CT scanner. From this viewpoint, any related art CT scanner, which is capable of moving a bed, on which a patient to be irradiated lies, in the body-axis direction and of adjusting the height of the bed, fails to examine adjustment of the position of an affected portion of the patient in the lateral direction (right and left direction of the body of the patient).

The positional adjustment of the related art CT scanner will be described more fully with reference to FIG. 16. FIG. 16 is a typical view showing a gantry portion of a related art CT scanner 1'. As shown in this figure, in a tunnel portion (detectable region) 1c' of a gantry 1b as a detector, the position of a CT bed 1a on which a patient B lies is adjusted, by vertical moving means (not shown), such that an affected portion (lesion) C is positioned at the center (shown by a chain line "j" in the figure) in the vertical direction (shown by an arrow "i" in the figure) of the tunnel portion 1c'. The position of the CT bed 1a in the tunnel portion 1c' is also adjusted such that a cross-sectional plane of the patient, which plane contains the affected portion (lesion) C and is perpendicular to the body-axis, can be scanned. Such adjustment of the CT bed 1a is performed by configuring the CT bed 1a as a mobile type CT bed movable in the body-axis direction, or configuring the CT scanner 1' as a mobile type CT scanner slid on moving rails installed on the floor face.

The related art CT scanner, however, fails to examine adjustment of the position of an affected portion in the right and left direction of the body of the patient, in a state that the patient lies on the bed, in the detectable region of the CT scanner, that is, in the direction perpendicular to the body-axis on the horizontal plane in the tunnel portion. In actual, since the diameter of the tunnel portion 1c' of the gantry 1b is generally set to about 1 m, it is difficult to adjust the position of the affected portion, that is, the position of the bed on which the patient lies in the lateral direction. As a result, if the affected portion C is located, as shown by an imaginary line (two-dot chain line) in the figure, at the center (shown by a chain line "k" in the figure) in the lateral direction (shown by an arrow "f" in the figure) of the tunnel portion 1c', the position of the affected portion C can be accurately checked; however, if the affected portion C is present at a side portion of the body of the patient B, and therefore, as shown by a solid line in the figure, the affected portion C is offset from the center (shown by the chain line "k" in the figure) of the lateral direction (shown by the arrow "f" in the figure) of the tunnel portion 1c', the position of the affected portion in the lateral direction is checked by any marking. Such checking of the position of the affected portion in the lateral direction by marking is undesirable.

BRIEF SUMMARY OF THE INVENTION

In view of the foregoing, the present invention has been made, and an object of the present invention is to provide a composite system for radiation therapy, which is capable of carrying a patient to be irradiated from a position of alignment of an affected portion to a position of irradiation thereof by linear movement and/or curved movement without the need of rotational movement of the common bed, and aligning, at the time of imaging or scanning of the target area or affected portion by a CT scanner, the center of the affected portion to the center of a detectable region of the CT scanner.

Another object of the present invention is to provide a composite system for radiation therapy including a common bed having an isocentric rotation mechanism, which system is capable of making use of the mechanism not only at the time of radiation therapy but also at the time of alignment performed by an inspection apparatus such as a CT scanner.

To achieve the above object, the present invention provides a composite system for radiation therapy, including: a CT scanner for checking the position of an affected portion or target area of a patient to be irradiated; an irradiation apparatus for disposing, on the basis of positional information of the affected portion checked by the CT scanner, the patient at a specific position at which the affected portion is aligned to an irradiation position, and performing irradiation to the affected portion; a common bed used for the CT scanner and the irradiation apparatus, in a state that the patient lies on the common bed, and moving means for moving the patient from the CT scanner to the specific position of the irradiation apparatus; wherein the moving means moves the patient on the common bed to the specific position by causing either of linear movement of the CT scanner and the irradiation apparatus, linear movement of the CT scanner and curved movement of the irradiation apparatus, curved movement of the CT scanner and the irradiation apparatus and linear movement of the CT scanner, linear movement of the CT scanner and the common bed, and linear movement of the CT scanner and curved movement of the common bed.

According to the feature of the composite system for radiation therapy in accordance with the present invention, it is possible to carry or transfer a patient to be irradiated from a position of alignment of an affected portion to a position of irradiation thereof without any rotation of the common bed, and hence to reduce a positional error caused by rotational movement.

The above-described composite system for radiation therapy has another effect. In the case of performing fine therapy in a three-dimensional space, an indication of the position of a lesion located at the deep of the body of a patient is often marked on the surface of the body by using a laser beam. In this regard, the related art moving mechanism using rotational movement is undesirable. The reason for this is as follows: namely, as described above, in the case where a patient is carried from a CT scanner to an irradiation apparatus by rotational movement of a bed on which the patient lies, it is relatively difficult to check whether or not the coordinate of the irradiation apparatus is joined entirely to the coordinate of the CT scanner. In other words, it is relatively difficult to confirm whether or not the position of the lesion marked by using a laser beam in the CT scanner is kept in the irradiation apparatus. On the contrary, according to the present invention, since a patient is carried from a CT scanner to an irradiation apparatus by linear movement and/or curved movement of the CT scanner, the irradiation apparatus and/or the common bed, it is possible to very simplify and facilitate to confirm that the coordinates of the CT scanner and the irradiation apparatus be joined to each other by using a laser beam, thereby improving the control of the positional accuracy of the lesion.

The moving means may include a moving mechanism for linearly moving the CT scanner and the irradiation apparatus, and preferably, the moving mechanism includes a linear moving mechanism for the CT scanner, and a linear moving mechanism for the irradiation apparatus, the linear moving mechanisms being disposed such that the movement directions of the CT scanner and the irradiation apparatus cross each other, more preferably, the linear moving mechanisms being disposed such that the movement directions of the CT scanner and the irradiation apparatus are perpendicular or substantially perpendicular to each other; and the common bed is disposed in the vicinity of a position to which the CT scanner and the irradiation apparatus are movable.

With this configuration, since a patient and its lesion are present in the same coordinate as that of the bed on which the patient lies, the lesion can be accurately irradiated by accurately checking the position of the lesion by the CT scanner having the moving mechanism, retracting or retreating the CT scanner while keeping the state of the bed as it is, and moving the irradiation apparatus having the moving mechanism to the patient on the bed such that the lesion is matched to an irradiation position. As a result, it is possible to reduce the movement of the bed between a position of alignment of an affected portion and a position of irradiation, and hence to perform radiation therapy without any movement of the bed. This makes it possible to significantly suppress occurrence of a positional error of an affected portion, and hence to accurately keep the position of a lesion in a three-dimensional space and thereby significantly improve the control of the therapy accuracy.

The moving means may further include a linear moving mechanism for the CT scanner, wherein the linear moving mechanism is movable in the same direction as the movement direction of the irradiation apparatus. With this configuration, at the time of CT scanning, the CT scanner can be moved to a position in front of the common bed by the linear moving mechanism in the same direction as the movement direction of the irradiation apparatus, and then the CT scanner can be advanced to the common bed, whereby the common bed is located a specific position of the CT scanner.

The moving means may include a moving mechanism for linearly moving the CT scanner and curvedly moving the irradiation apparatus, and preferably, the moving mechanism includes a linear moving mechanism for the CT scanner so as to be movable to or from the common bed, and a curvedly moving mechanism for the irradiation apparatus so as to be movable in the circumferential direction around the common bed, for example, in the circumferential direction centered at the common bed.

With this configuration, it is possible to perform irradiation to a lesion of a patient by accurately checking the position of the lesion by the CT scanner having the moving mechanism, retracting the CT scanner while keeping the state of the patient as it is, and moving the irradiation apparatus having the moving mechanism, which is movable curvedly through the vicinity of the common bed in the circumferential direction around the common bed, for example, in the circumferential direction centered at the common bed, to the patient such that the lesion is matched to an irradiation position. This composite system also makes it possible to reduce the movement of the bed between a position of alignment of an affected portion and a position of irradiation thereof, and hence to perform radiation therapy without any movement of the bed.

The moving means may include a moving mechanism for curvedly moving the CT scanner and the irradiation apparatus and linearly moving the CT scanner; and preferably, the moving mechanism includes curvedly moving mechanisms for the CT scanner and the irradiation apparatus so as to be movable in the circumferential direction around the common bed respectively, for example, in the circumferential directions centered at the common bed or in the circumferential directions around the common bed which is positioned between the center of the movement circle of the CT scanner and the irradiation apparatus and circular-arc depicted by the moving mechanisms, and also comprises a linear moving mechanism for the CT scanner, wherein when the common bed is located in front of the CT scanner, the CT scanner is movable along the longitudinal direction to the common bed by the linear moving mechanism.

With this configuration, the CT scanner having been moved to a position in front of the common bed by the curvedly moving mechanism can be advanced to the common bed side by the linear moving mechanism in such a manner that the common bed reaches a specific position of the CT scanner, to accurately confirm the position of a lesion, and in such a state, the CT scanner can be retreated and curvedly moved, and the irradiation apparatus including the curvedly moving mechanism for curvedly moving the irradiation apparatus in the circumferential direction around the common bed can be moved in accordance with the positional information of the lesion of the patient, to irradiate the lesion with radiation. This composite system also makes it possible to reduce the movement of the bed between a position of alignment of an affected portion and a position of irradiation thereof, and hence to perform radiation therapy without any movement of the bed.

The moving means may include a moving mechanism for linearly moving the CT scanner and the common bed; and preferably, the moving mechanism includes a linear moving mechanism for the CT scanner, and a linear moving mechanism for the common bed, the linear moving mechanisms being disposed such that the movement directions of the CT scanner and the common bed cross each other, more preferably, the linear moving mechanisms being disposed such that the movement directions of the CT scanner and the common bed are perpendicular or substantially perpendicular to each other, wherein the CT scanner is disposed in parallel to the irradiation apparatus, and the common bed is movable between the CT scanner and the irradiation apparatus.

With this configuration, at the time of alignment of a lesion of a patient, the common bed may be moved to the CT scanner and also the CT scanner be advanced to the common bed, and at the time of irradiation, the CT scanner may be retracted from the common bed and also the common bed be moved to the irradiation apparatus, with a result that it is possible to carry the patient from the CT scanner to the irradiation apparatus without any rotational movement of the common bed on which the patient lies.

The moving means may include a moving mechanism for linearly moving the CT scanner and curvedly moving the common bed; and preferably, the moving mechanism includes a curvedly moving mechanism for the common bed, wherein the CT scanner and the irradiation apparatus are disposed in the vicinity of a curve along which the common bed is movable by the curvedly moving mechanism, and also includes a linear moving mechanism for the CT scanner, wherein when the common bed is located in front of the CT scanner, the CT scanner is movable along the longitudinal direction to the common bed by the linear moving mechanism.

With this configuration, at the time of alignment of a lesion of a patient, the common bed may be moved to the CT scanner and also the CT scanner be advanced to the common bed, and at the time of irradiation, the CT scanner may be retracted from the common bed and also the common bed be moved to the irradiation apparatus, with a result that it is possible to carry the patient from the CT scanner to the irradiation apparatus without any rotational movement of the common bed on which the patient lies. Therefore, it may be regarded that the patient is moved in only one coordinate.

Here, as the curvedly moving mechanism for the common bed, there may be used a mobile mechanism using curved rails, a sliding mechanism using a sliding floor curvedly movable, or a mechanism configured such that a turn table on which the common bed is mounted is installed on a floor face. The curved movement of the common bed can be smoothly performed by fixedly mounting the common bed to the turn table. Also, if the common bed has the isocentric rotation mechanism, the turn table can easily make use of the isocentric rotation mechanism of the common bed.

The common bed preferably has an isocentric rotation mechanism.

With this configuration, not only for the composition system for radiation therapy, which allows the patient to be irradiated to lie at the specific position without movement of the common bed, but also for the composite system for radiation therapy, which is capable of moving the common bed, since the isocentric rotation mechanism can be moved along with the common bed not by rotating the common bed but by linearly or curvedly moving the common bed, the isocentric rotation mechanism of the common bed can be effectively used at the time of scanning of the CT scanner.

The composite system for radiation therapy may further include an X-ray simulator, wherein the moving means preferably further includes a moving mechanism for further moving the patient on the common bed to a specific position of the X-ray simulator by causing either of linear movement of the CT scanner, the irradiation apparatus and the X-ray simulator, linear movement of the CT scanner and curved movement of the irradiation apparatus and the X-ray simulator, curved movement of the CT scanner, the irradiation apparatus and the X-ray simulator and linear movement of the CT scanner, linear movement of the CT scanner and the common bed, and linear movement of the CT scanner and curved movement of the common bed.

With this configuration, it is possible to further move or transfer the patient on the common bed to a specific position of the X-ray simulator, with a result that it can be checked by the X-ray simulator whether or not the aligned position by the CT scanner is deviated due to the fact that the affected portion is moved in the body, for example, by breath of the patient, and if deviated, the aligned position can be corrected on the basis of the checked result inputted in, for example, a position control mechanism, followed by return of the patient again to the irradiation apparatus side by linear movement and/or curved movement. As a result, it is possible to further improve the accuracy in positional correction.

As described above, if the common bed of the composite system of the present invention has the isocentric rotation mechanism, the isocentric rotation mechanism can be used for the X-ray simulator. In particular, the positioning by the X-ray simulator has been three-dimensionally performed by matching three-dimensional data obtained by CT scanning with the obtained two-dimensional image by computer processing, and accordingly, if the isocentric rotation mechanism can be used for the X-ray simulator, it is possible to easily perform the three-dimensional positioning, and hence to further improve the positioning accuracy.

The moving means may preferably include 1) a moving mechanism for linearly moving the CT scanner, the irradiation apparatus and the X-ray simulator; and the moving mechanism includes a linear moving mechanism for the CT scanner, a linear moving mechanism for the irradiation apparatus, and a linear moving mechanism for the X-ray simulator, the linear moving mechanisms being disposed such that the movement direction of the CT scanner and the movement direction of the irradiation apparatus and the X-ray simulator cross each other, more preferably, such that the movement direction of the CT scanner and the movement direction of the irradiation apparatus and the X-ray simulator are perpendicular or substantially perpendicular to each other, and the common bed is disposed in the vicinity of a position to which the CT scanner, the irradiation apparatus and the X-ray simulator are movable, 2) a moving mechanism for linearly moving the CT scanner, the irradiation apparatus and the X-ray simulator; and the moving mechanism includes a linear moving mechanism for the CT scanner, a linear moving mechanism for the irradiation apparatus and a linear moving mechanism for the X-ray simulator, the linear moving mechanisms being disposed such that the movement direction of the CT scanner and the movement direction of the irradiation apparatus and the X-ray simulator cross each other, more preferably, such that the movement direction of the CT scanner and the movement direction of the irradiation apparatus and the X-ray simulator are perpendicular or substantially perpendicular to each other, and the common bed is disposed in the vicinity of a position to which the CT scanner, the irradiation apparatus and the X-ray simulator are movable, and the CT scanner further includes a linear moving mechanism movable in same direction as the movement direction of the irradiation apparatus and the X-ray simulator, 3) a moving mechanism for linearly moving the CT scanner and curvedly moving the irradiation apparatus and the X-ray simulator; and the moving mechanism includes a linear moving mechanism for the CT scanner so as to be movable to or from the common bed, curvedly moving mechanisms for the irradiation apparatus and the X-ray simulator so as to be movable in the circumferential directions around the common bed respectively, for example, in the circumferential directions centered at the common bed, 4) a moving mechanism for curvedly moving the CT scanner, the irradiation apparatus and the X-ray simulator, and linearly moving the CT scanner; and the moving mechanism includes curvedly moving mechanisms for the CT scanner, the irradiation apparatus and the X-ray simulator so as to be movable in the circumferential directions around the common bed respectively, for example, in the circumferential directions centered at the common bed or in the circumferential directions around the common bed which is positioned between the center of the movement circle of the CT scanner, the irradiation apparatus and the X-ray simulator and the circular-arc depicted by the curvedly moving mechanisms, and also includes a linear moving mechanism for the CT scanner, wherein when the common bed is located in front of the CT scanner, the CT scanner is movable along the longitudinal direction to the common bed by the linear moving mechanism, 5) a moving mechanism for linearly moving the CT scanner and the common bed; and the moving mechanism includes a linear moving mechanism for the CT scanner, and a linear moving mechanism for the common bed, the linear moving mechanisms being disposed such that the movement directions of the CT scanner and the common bed cross each other, more preferably, such that the movement directions of the CT scanner and the common bed are perpendicular or substantially perpendicular to each other, wherein the CT scanner is disposed in parallel to the irradiation apparatus, the irradiation apparatus is disposed in parallel to the X-ray simulator, and the common bed is movable between the CT scanner, the irradiation apparatus and the X-ray simulator, or 6) a moving mechanism for linearly moving the CT scanner and curvedly moving the common bed; and the moving mechanism includes a curvedly moving mechanism for the common bed, wherein the CT scanner, the irradiation apparatus and the X-ray simulator are disposed in vicinity of a curve along which the common bed is movable by the curvedly moving mechanism, and also includes a linear moving mechanism for the CT scanner, wherein when the common bed is located in front of the CT scanner, the CT scanner is movable along the longitudinal direction to the common bed by the linear moving mechanism.

With these configurations, the patient to be irradiated, who lies on the common bed, can be further located at a specific position of the X-ray simulator with a high positional accuracy, without the need of rotation of the common bed. Further, if the common bed has the isocentric rotation mechanism, as described above, according to the present invention, the isocentric rotation mechanism of the common bed can be used for the X-ray simulator.

The composite system for radiation therapy in accordance with the present invention, the detectable region (a tunnel portion of a gantry) of the CT scanner preferably has a diameter ranging from 1.5 to 3 m, and more preferably, the positional adjustment means for adjusting the position of a patient in the lateral direction (right and left direction of the patient who lies on the bed) in a detectable region of the CT scanner is additionally provided. With this configuration, the position of an affected portion of a patient on the bed can be checked by preliminary scanning before scanning of the cross-sectional plane containing the affected portion. Accordingly, if the affected portion is deviated from the center in the lateral direction at the tunnel portion of a gantry, the position of the affected portion can be adjusted not only in the vertical direction and the body-axis direction but also in the lateral direction of the tunnel portion, with a result that the affected portion can be positioned at the center of the CT scanner at the time of scanning of the cross-sectional plane containing the affected portion by the CT scanner.

If the common bed has the isocentric rotation mechanism, as described above, according to the present invention, the isocentric rotation mechanism of the common bed can be used for the CT scanner. In this case, the isocentric rotation mechanism is allowed to effectively function by setting the diameter of the tunnel portion of the gantry of the CT scanner to the above-described size. In addition, the CT scanner in which the diameter of the tunnel portion of the gantry is set to the above-described size is useful for a CT scanner (for example, CT scanner disposed in a room separated from a room in which an irradiation apparatus is provided) other than that of the composite system of the present invention, and more specifically, effectively usable as a CT scanner of a composite system using the above-described rotary bed.

The present invention further provides a composite system for radiation therapy, including: a CT scanner for checking the position of an affected portion of a patient to be irradiated; an irradiation apparatus for disposing, on the basis of positional information of the affected portion checked by the CT scanner, the patient at a specific position at which the affected portion is aligned to an irradiation position, and performing irradiation to the affected portion; a common bed used for the CT scanner and the irradiation apparatus, in a state that the patient lies on the common bed, and moving means for moving the patient from the CT scanner to the specific position of the irradiation apparatus; wherein the moving means moves the patient on the common bed by causing linear movement of the CT scanner, the irradiation apparatus and the common bed; and the moving mechanism includes a linear moving mechanism for the CT scanner, and a linear moving mechanism for the irradiation apparatus, the linear moving mechanisms being disposed such that the movement directions of the CT scanner and the irradiation apparatus cross each other, more preferably, the movement directions of the CT scanner and the irradiation apparatus are perpendicular or substantially perpendicular to each other, a first bed used for the CT scanner, a second bed used for the irradiation apparatus, and a moving member for linearly moving the common bed, wherein the common bed is placed on the upper surface of at least one of the first bed and the second bed disposed in series, and is linearly moved between the upper surface of the first bed and the upper surface of the second bed by the moving member.

With this configuration, at the time of alignment of a lesion, the common bed may be placed on the first bed of the CT scanner and also the CT scanner may be advanced to the common bed on the first bed, and at the time of irradiation, the CT scanner may be retracted from the common bed on the first bed, the common bed may be moved to the second bed of the irradiation apparatus and also the irradiation apparatus may be moved to the second bed. As a result, it is possible to carry the patient from the CT scanner to the irradiation apparatus without any rotational movement of the common bed on which the patient lies, and hence to reduce a positional error by rotational movement.

Preferably, the composite system for radiation therapy further includes an X-ray simulator; wherein the moving means further includes a moving mechanism for further moving the patient on common bed to a specific position of the X-ray simulator by causing linear movement of the CT scanner, the irradiation apparatus, the common bed and the X-ray simulator; and the moving mechanism includes a linear moving mechanism for the CT scanner, a linear moving mechanism for the irradiation apparatus and a linear moving mechanism for the X-ray simulator, the linear moving mechanisms being disposed such that the movement direction of the CT scanner and the movement direction of the irradiation apparatus and the X-ray simulator cross each other, more preferably, the movement direction of the CT scanner and the movement direction of the irradiation apparatus and the X-ray simulator are perpendicular or substantially perpendicular to each other, and a first bed used for the CT scanner, a second bed used for the irradiation apparatus, the second bed is also used for X-ray simulator, and a moving member for linearly moving the common bed, wherein the common bed is placed on the upper surface of at least one of the first bed and the second bed disposed in series, and is linearly moved between the upper surface of the first bed and the upper surface of the second bed by the moving member.

With this configuration, the patient to be irradiated, who lies on the common bed which is placed on the second bed, can be further located at a specific position of the X-ray simulator by the moving mechanism for the X-ray simulator with a high positional accuracy, without the need of rotation of the common bed.

In addition, to smoothly, linearly move the common bed on the first and second beds, the moving member is preferably configured as a set of rollers, a set of wheels, a combination of rails and a sliding portion mounted on the moving rails, or a conveyor.

BRIEF DESCRIPTION OF THE SEVERAL VIEWS OF THE DRAWINGS

The above and other objects, features and advantages of the present invention will be apparent from the following detailed description of the preferred embodiments of the present invention in conjunction with the accompanying drawings, in which.

DETAILED DESCRIPTION OF THE INVENTION

Hereinafter, preferred embodiments of the present invention will be described in detail with reference to the drawings.

Embodiment 1

Figure 1:
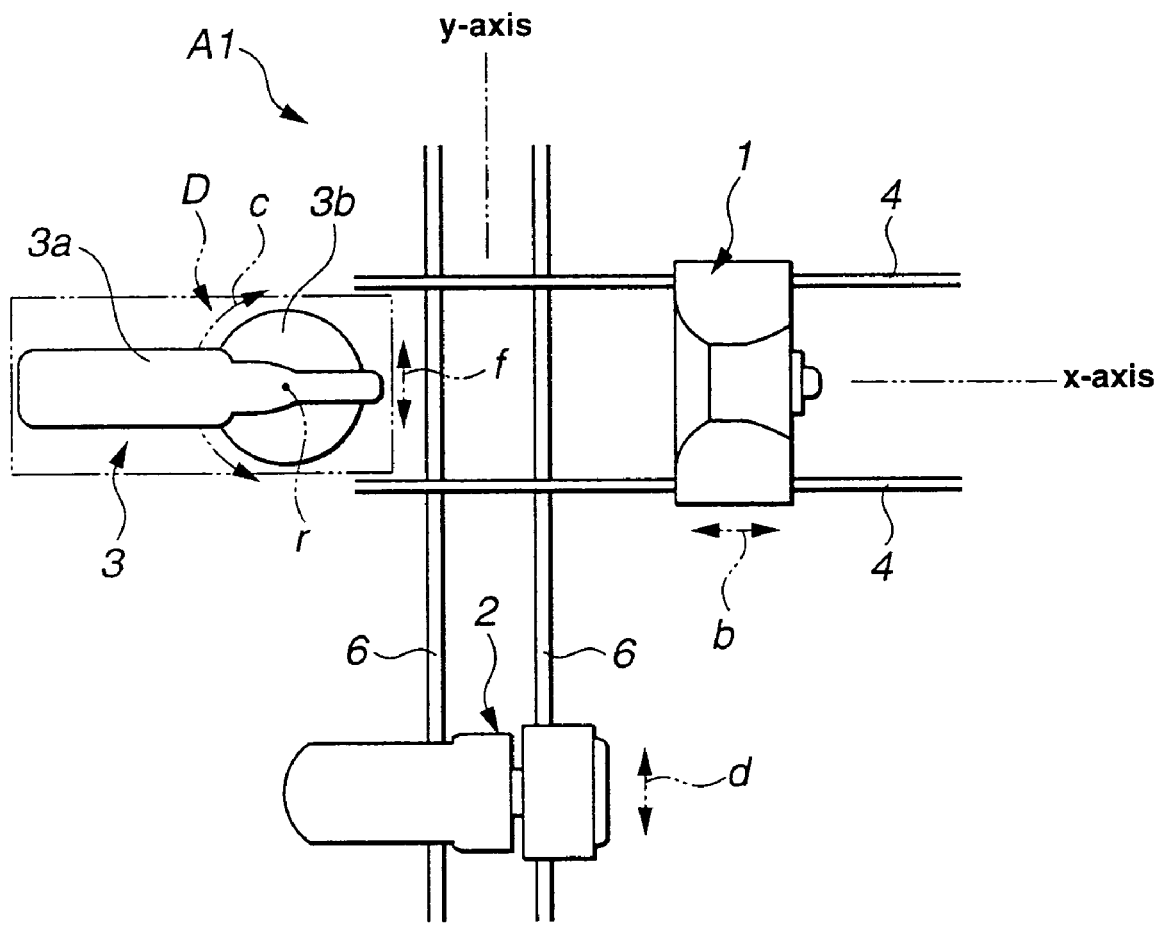
FIG. 1 is a schematic plan view of a first embodiment of a composite system for radiation therapy according to the present invention.

A first embodiment of a composite system for radiation therapy according to the present invention will be described with reference to FIG. 1. FIG. 1 is a schematic plan view, as seen from above, of a composite system A1 for radiation therapy according to the first embodiment of the present invention.

The composite system A1 for radiation therapy includes a CT scanner 1 having a linear moving mechanism and an irradiation apparatus 2 having a linear moving mechanism. The CT scanner 1 and the irradiation apparatus 2 are disposed in the same room (therapy room) in a state that the movement direction of the CT scanner 1 is perpendicular to that of the irradiation apparatus 2. Here, according to the present invention, the movement direction of the CT scanner 1 may cross diagonally that of the irradiation apparatus 2, however, more preferably, the movement directions of the CT scanner 1 and the irradiation apparatus 2 are perpendicular or substantially perpendicular to each other.

A common bed 3 used in common for the CT scanner 1 and the irradiation apparatus 2 is disposed at a position at which the common bed 3 becomes usable by the movement of the CT scanner 1 and the irradiation apparatus 2, and more specifically, it is disposed within moving ranges of the CT scanner 1 and the irradiation apparatus 2, in other word, the common bed 3 is disposed in the vicinity of a position to which the CT scanner 1 and the irradiation apparatus 2 are movable. The moving directions of the CT scanner 1 and the irradiation apparatus 2 cross each other, in this embodiment, the directions are perpendicular to each other. In this embodiment, the common bed 3 is disposed in the vicinity of a position (intersection) at which the moving directions of the CT scanner 1 and the irradiation apparatus 2 are perpendicular to each other.

In this embodiment and later embodiments, a computer control system (not shown), which is operated to manage and control a series of operations in a wide range from an alignment operation performed based on measurement results obtained by the CT scanner 1 to an irradiation operation performed by the irradiation apparatus 2, is provided in the therapy room or an operating room provided separately from the therapy room. The computer control system includes, for example, a control unit for the CT scanner 1, an operating unit for controlling display of measurement results, images, and the like obtained by the CT scanner 1, and a control unit for the irradiation apparatus 2.

The moving mechanisms used for each of the CT scanner 1 and the irradiation apparatus 2 of the composite system A1 for radiation therapy are not particularly limited but may be configured as follows. Examples of the linear moving mechanisms for the CT scanner 1 include a mobile mechanism such as a floor face mobile mechanism, a ceiling mobile mechanism (not shown), or a wall face mobile mechanism (not shown); and a sliding mechanism. The floor face mobile mechanism includes two CT scanner rails 4 installed on a floor face 5 (see FIG. 15) of a therapy room, wherein a drive portion (for example, motor) is driven by a computer (not shown), to allow the CT scanner 1 to be moved on the rails 4 in a line direction (shown by an arrow "b" in the figure), that is, the x-axis direction in the figure. The ceiling mobile mechanism (not shown) includes rails installed on a ceiling in place of the floor face. The wall face mobile mechanism includes rails installed on wall faces of wall bodies provided on both side surfaces of the CT scanner 1 in place of the floor face. The sliding mechanism includes a sliding floor (not shown) on which the CT scanner 1 is mounted, wherein a drive portion (for example, motor) is driven by control of a computer (not shown), to allow the sliding mechanism to be moved in a line direction (shown by the arrow "b" in the figure), that is, in the x-axis direction in the figure.

Meanwhile, examples of the linear moving mechanisms for the irradiation apparatus 2 include a mobile mechanism such as a floor face mobile mechanism, a ceiling mobile mechanism (not shown), or a wall face mobile mechanism (not shown); and a sliding mechanism. The floor face mobile mechanism includes two rails 6 for the irradiation apparatus may be installed on the floor face 5 (see FIG. 15) of the therapy room in such a manner as to extend in the direction perpendicular to that of the rails 4 for the CT scanner, wherein a drive portion (for example, motor) is driven by a computer (not shown), to allow the irradiation apparatus 2 to be moved on the rails 6 in the line direction (shown by an arrow "d"), that is, the y-axis direction in the figure. The ceiling mobile mechanism (not shown) includes rails installed on a ceiling in place of the floor face. The wall face mobile mechanism includes rails installed on wall faces of wall bodies provided on both side surfaces of the irradiation apparatus 2 in place of the floor face. The sliding mechanism includes a sliding floor (not shown) on which the irradiation apparatus 2 is mounted, wherein a drive portion (for example, motor) is driven by control of a computer (not shown), to allow the sliding mechanism to be moved in a line direction (shown by the arrow "d" in the figure), that is, in the y-axis direction in the figure. It is to be noted that the two rails 6 for the irradiation apparatus 2 may be replaced with only one rail.

In the case of using the sliding mechanism including the sliding floor as the moving mechanism in this embodiment and later embodiments, the sliding floor may be configured as a bellows floor to reduce the irregularities of a floor face of a therapy room.

In this embodiment and later embodiments, the moving mechanisms of the CT scanner, irradiation apparatus, common bed, and X-ray simulator are preferably contrived so as to prevent the interference of the movements thereof with each other. For example, in the case where the moving range of the CT scanner crosses the moving range of the irradiation apparatus as in the composite system for radiation therapy, if the above-described mobile mechanisms are used as the linear moving mechanisms for the CT scanner and the irradiation apparatus, it is preferred that if one of the mobile mechanism is the floor face mobile mechanism, the other be selected as the wall surface or ceiling mobile mechanism. Accordingly, with respect to rails shown in FIG. 1 and later figures, either of the floor face mobile mechanism, wall face mobile mechanism, ceiling mobile mechanism, and the sliding mechanism using the sliding floor can be selectively used even unless otherwise specified. In addition, the length of rails, and the gap between two rails are not limited to those shown in the figure but may be suitably selected depending on the size and arrangement of the composite system.

Figure 13:
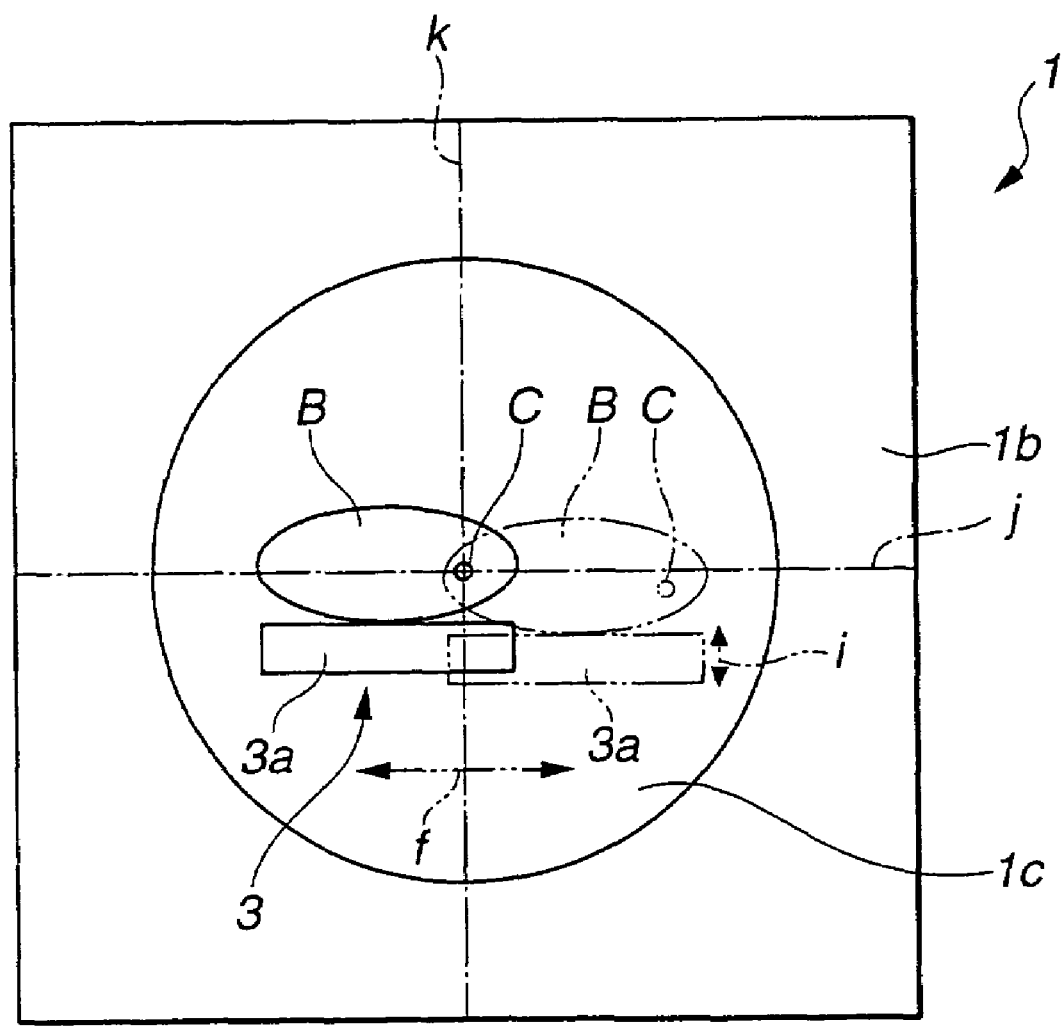
FIG. 13 is a view illustrating a configuration of a CT scanner suitably used for the composite system for radiation therapy according to the present invention.
Figure 14:
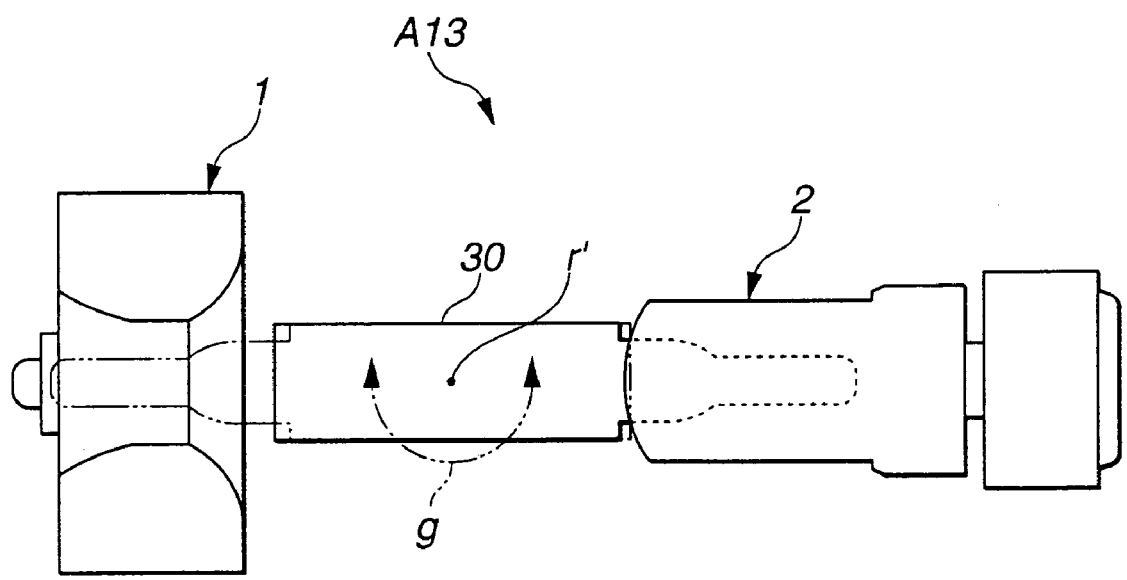
FIG. 14 is a schematic plan view of a related art composite system for radiation therapy.

According to the present invention, the CT scanner 1 may be represented by any generally used CT scanner; however, in this embodiment and later embodiments, to more accurately perform alignment of an affected portion (lesion), the CT scanner 1 may be configured as shown in FIG. 13. FIG. 13 typically shows a portion of a detector (gantry) 1b of a preferred example of the CT scanner 1. The CT scanner 1 shown in FIG. 13 includes positional adjustment means (not shown) for adjusting the position of a patient B to be irradiated in the lateral direction, in a tunnel portion 1c of the gantry 1b as a detectable region of the CT scanner 1, thereby more accurately performing alignment of an affected portion (lesion) C of the patient B. To be more specific, as shown in FIG. 13, the diameter of the tunnel portion 1c of the gantry 1b as the detector of the CT scanner 1 is set to be larger than that of a conventional one in order to make a common bed 3 on which the patient B lies is placed movable in the tunnel portion 1c in the lateral direction, that is, in a direction shown by an arrow "f" in the figure. Concretely, the diameter of the tunnel portion 1c is preferably in a range of about 1.5 to 3 m, more preferably, in a range of about 2 to 2.5 m.

The positional adjustment means for adjusting the position of the patient B in the lateral direction in the tunnel portion 1c of the CT scanner 1 shown in FIG. 13 is not particularly limited but may be represented by any movement means (or adjustment means) known in the art. For example, the positional adjustment means may be configured such that the common bed 3 includes a position adjusting mechanism (not shown) such as a sliding mechanism which supports a top plate 3a slidably in the upper surface of the common bed 3, wherein a drive mechanism (not shown) contained in the sliding mechanism is driven by control of a computer (not shown) on the basis of preliminary scan data of the CT scanner, to allow the top plate 3a, on which the patient to be irradiated lies, to be slid in the right-and-left direction of the body of the patient (in the lateral direction shown by an arrow "f" in the figure).

With this configuration, even if the affected portion (lesion) C of the patient B is largely offset from the center of the body in the lateral direction, for example, present near one end side of the body in the lateral direction as shown by an imaginary line (two-dot chain line), the affected portion C can be moved to the center of the tunnel portion 1c in the lateral direction by the sliding mechanism. After that, if needed, the position of the affected portion (lesion) C of the patient B in the height direction may be adjusted in accordance with a usual manner of adjusting the height of the bed in the vertical direction (shown by an arrow "i" in the figure) by using movement means (or adjustment means) used for a related art CT scanner. Consequently, as shown by a solid line in FIG. 13, the center position of the affected portion (lesion) C is aligned to the center position (intersection between chain lines "j" and "k") of the detectable region (tunnel portion 1c of the gantry 1b) of the CT scanner 1; By operating the CT scanner in such a state, the center of a cross-sectional plane to be scanned with the CT scanner corresponds to the center of the affected portion (lesion) C. Accordingly, upon radiation therapy for tumor or the like, the affected portion (lesion) can be detected at the center of gantry of the CT scanner 1 irrespective of the position of the affected portion, with a result that the position of the affected portion can be very accurately recognized, to be thus desirably irradiated.

In this embodiment and later embodiments, the irradiation apparatus 2 may be represented by any generally used irradiation apparatus, for example, the linear accelerator (such as robotic arm linear accelerator, C-arm linear accelerator).

As the common bed 3 used for the composite system A1 for radiation therapy and composite systems A2 to A10 for radiation therapy to be described later, there is preferably used a common bed having an isocentric rotation mechanism D enabling positional adjustment in the circular direction (shown by an arrow "c" in the figure) so as to change the center of field of irradiation and the angle of irradiation.

Figure 15:
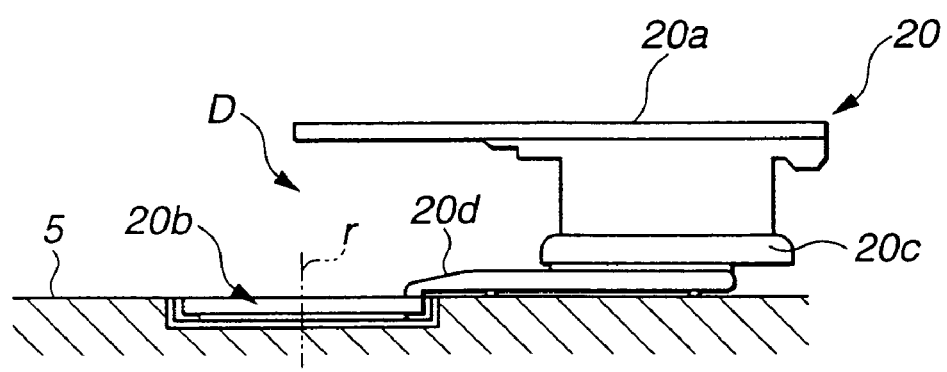
FIG. 15 is a schematic side view illustrating a configuration of an isocentric rotation mechanism provided for a bed which is used for the radiation therapy apparatus.
Figure 16:
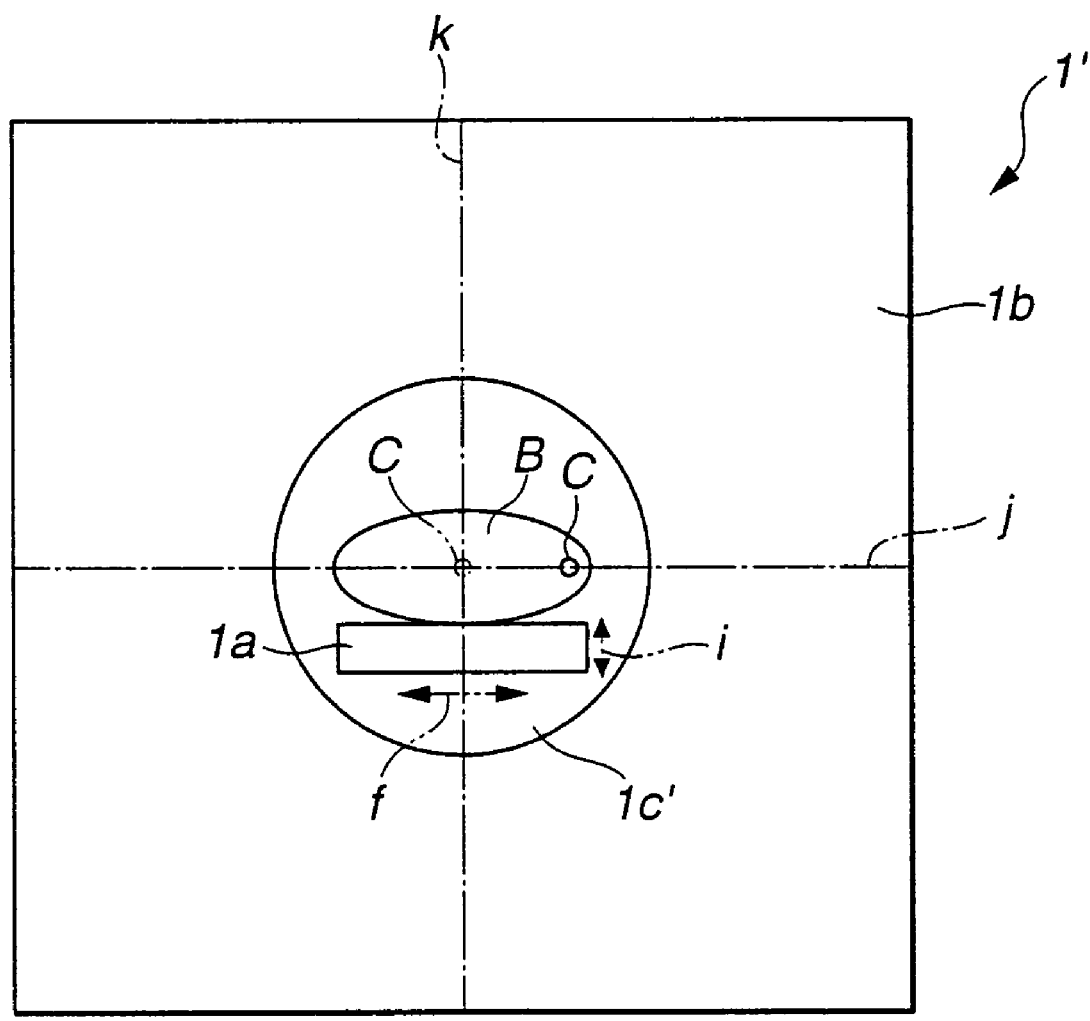
FIG. 16 is a view illustrating a configuration of a related art CT scanner.

To be more specific, like the therapy bed 20 shown in FIG. 15, a turn table 3b (shown by reference numeral 20b in FIG. 15) is provided on the floor face at a position in the vicinity of the leading end side (end portion on the used apparatus side) of the common bed 3 shown in FIG. 1 in such a manner that an isocenter "r" is set to the rotational center. The leading end side (end portion on the used apparatus side in a state directed nearly forwardly to the apparatus) of a rotational disk (not shown in FIG. 1 but shown by reference numeral 20d in FIG. 15) is fixed to the peripheral edge of the turn table 3b in such a manner that the rotational disk is rotatable integrally with the turn table 3b. A base (not shown in FIG. 1 but shown by reference numeral 20c in FIG. 15) of the common bed 3 is mounted on the rotational disk. With this configuration, the common bed 3 is connected to the turn table 3b in such a manner as to be horizontally rotatable together with the turn table 3b, and thereby it has the isocentric rotation mechanism D. The common bed 3 preferably includes, in addition to the isocentric rotation mechanism D, a mechanism allowing the positional adjustment of the top plate 3a (20a in FIG. 15) in the lateral direction (shown by an arrow "f") with respect to the used apparatus, thereby allowing the positional adjustment of the common bed 3 in the lateral direction in the tunnel portion of the CT scanner as described above, and also includes mechanisms enabling the positional adjustment in the longitudinal direction and in the height direction. A preferred example of such a common bed 3 is a therapy bed used for the irradiation apparatus. In addition, according to the present invention, the common bed preferably has the above-described isocentric rotation mechanism; however, the configuration of the isocentric rotation mechanism is not particularly limited, and any other isocentric rotation mechanism having a configuration other than that described above insofar as the mechanism is rotatable in the direction shown by the arrow "c".

According to the composite system A1 for radiation therapy in this embodiment, the patient to be irradiated usually lies on the common bed 3, and the CT scanner 1 is linearly moved in the minus direction of the x-axis in the figure (the left direction in the figure), to accurately check the position of a lesion of the patient, and then the mobile type CT scanner 1 is linearly moved in the plus direction of the x-axis in the figure (the right direction in the figure) to be thus retracted. After that, the irradiation apparatus 2 is linearly moved to the position of the lesion of the patient in the plus direction of the y-axis in the figure (the upward direction in the figure) to perform irradiation to the lesion of the patient on the basis of the positional data checked by the CT scanner 1. In this way, according to the composite system A1 for radiation therapy in this embodiment, it is possible to reduce the degree of the movement of the bed between a position for alignment and a position for irradiation.

Accordingly, it is possible to solve the related art problem associated with the rotational movement of a bed from alignment of an affected portion and radiation therapy for the affected portion, and hence to eliminate an error caused along with the rotational movement of the bed. In addition, if the linear moving mechanisms for the CT scanner and the irradiation apparatus are controlled by a computer as described above, the CT scanner and the irradiation apparatus can be accurately, linearly moved to a specific position on the basis of a command from the computer.

In addition to the above-described advantage of this embodiment, if the CT scanner 1 is, as described above, configured to make the position of the affected portion of the patient to be irradiated adjustable (or movable) in the lateral direction in the detectable region, since the diameter of the tunnel portion of the gantry of the CT scanner is as described above and the positional adjustment means is provided for the CT scanner by such configuration that as described above, there can be obtained the following advantage. At the time of performing CT scanning, for the patient to be irradiated on the common bed 3, first, an ordinary cross-sectional image in the direction perpendicular to the body-axis of the patient or an image converted therefrom is prepared on the basis of preliminary CT scanning data and is displayed on a display screen, and then, on the basis of the image displayed on the display screen, the position of the common bed 3 in the lateral direction and, if needed, in the height direction is adjusted by a bed position control mechanism in such a manner that the center of an affected portion (lesion) of the patient is aligned to the center axis of a cross-section along which CT scanning is to be performed. In this state, CT scanning is performed, to check whether or not the affected portion (lesion) to be irradiated is accurately aligned to the center of the tunnel portion 1c (see FIG. 13) of the gantry 1b (see FIG. 13) of the CT scanner 1. At the time of irradiation, on the basis of the positional data checked by the CT scanner 1, the common bed 3 on which the patient lies is disposed at a specific position for the irradiation apparatus 2 by control of a computer (not shown). With this operation, the position of the affected portion (lesion) of the patient can be detected without occurrence of any error, and the affected portion can be accurately subjected to radiation therapy. This makes it possible to enhance the accuracy of radiation therapy and facilitate the control of the accuracy thereof. Accordingly, the use of the CT scanner described in this embodiment is advantageous in that since the center of an affected portion (lesion) of a patient to be irradiated can be aligned to an actual origin in a three-dimensional space in the radiation therapy room, it is possible to eliminate an error, which has been caused along with alignment of the affected portion (lesion), and hence to significantly enhance the therapy accuracy and facilitate the control of the therapy accuracy.

Further, as shown in FIG. 1, when the CT scanner 1 is disposed on the leading end side (on the turn table 3b side) of the common bed 3, the isocentric rotation mechanism D of the common bed 3 can be used for the irradiation apparatus 2 and the CT scanner 1. This is advantageous in further enhancing the therapy accuracy and the control of the therapy accuracy. Here, if the diameter of the tunnel portion of the gantry of the CT scanner is as described above, the positional adjustment of the affected portion in the gantry is facilitated by making use of the isocentric rotation mechanism of the common bed 3.

Embodiment 2

Figure 2:
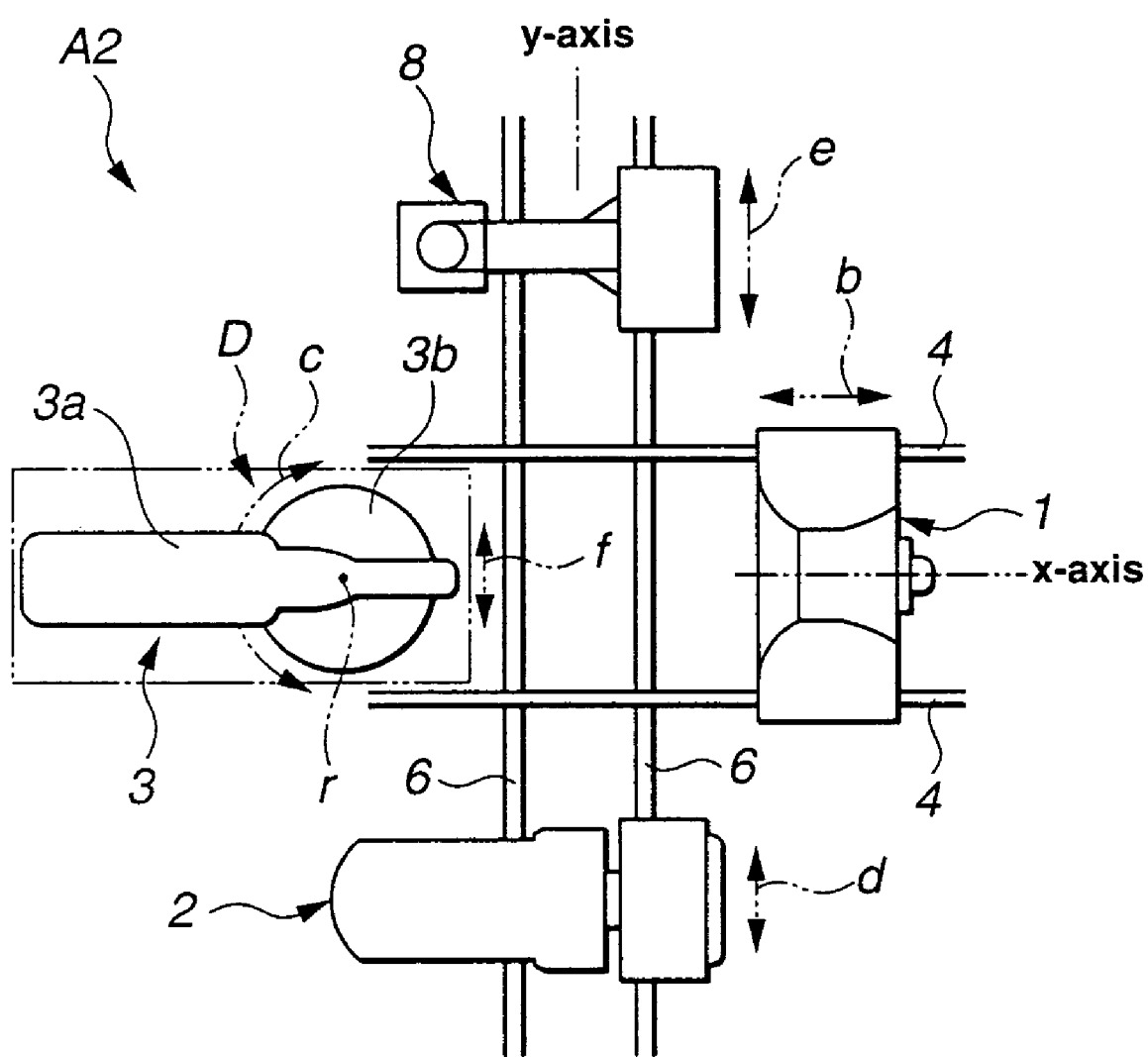
FIG. 2 is a schematic plan view of a second embodiment of the composite system for radiation therapy according to the present invention.

A second embodiment of the composite system for radiation therapy according to the present invention will be described with reference to FIG. 2. Referring to FIG. 2, there is shown a composite system A2 for radiation therapy according to the second embodiment. The composite system A2 for radiation therapy in this embodiment includes, in addition to the configuration of the composite system A1 for radiation therapy according to the first embodiment, an X-ray simulator 8 including a moving mechanism. To be more specific, if the linear moving mechanism for the irradiation apparatus 2 is of type using the rails 6, the rails 6 for the irradiation apparatus 2 are further extended, and the X-ray simulator 8 including the moving mechanism is provided so as to be movable on the rails 6 extending in the same line direction (shown by an arrow "e" in the figure) as the movement direction of the irradiation apparatus 2, that is, in the y-axis direction in the figure by control of a computer (not shown). The common movement direction of the irradiation apparatus 2 (which is the same as that used for the composite system A1 for radiation therapy), and in this embodiment, the X-ray simulator 8 is thus perpendicular to the movement direction of the CT scanner 1 (which is the same as that used for the composite system A1 for radiation therapy). Even in this embodiment, the linear moving mechanism for the X-ray simulator 8 is not limited to the mobile mechanism using the rails but may be configured as the above-described sliding mechanism for sliding the moving base as the sliding floor. Also, even in this embodiment, the same common bed 3 as that used in the composite system A1 for radiation therapy may be used preferably.

Even in the composite system A2 for radiation therapy according to this embodiment, in addition to the above-described function of the composite system A1 for radiation therapy, an additional function of checking a deviation in position of an affected portion of a patient can be obtained. To be more specific, by interrupting the irradiation, and retracting the irradiation apparatus 2 by the linear moving mechanism for the irradiation apparatus 2 in the minus direction of the y-axis in the figure (the downward direction in the figure) and then moving the X-ray simulator 8 to the position in front of the common bed 3 by the linear moving mechanism for the X-ray simulator 8 in the minus direction of the y-axis (in the downward direction in the figure) by control of a computer (not shown), it can be checked, as described above, by the X-ray simulator 8 whether or not the affected portion of the patient is deviated from the aligned position obtained by the CT scanner due to the fact that the affected portion is moved in the body, for example, by breath of the patient.

If the common bed 3 has the isocentric rotation mechanism D, it is possible to use the isocentric rotation mechanism D for the X-ray simulator 8. Accordingly, it becomes possible to check more accurately whether or not an affected portion of a patient is deviated from the aligned position.

After the checking by the X-ray simulator 8, both the X-ray simulator 8 and the irradiation apparatus 2 may be returned to the original positions by control of a computer (not shown). With this configuration, it is possible to re-start the irradiation to the affected portion in the state that the position of the affected portion has been accurately corrected. In addition, if the CT scanner 1 in the composite system A2 for radiation therapy in this embodiment is configured as that used for the composite system A1 for radiation therapy, that is, configured so as to make the position of the affected portion of the patient adjustable in the lateral direction in the detectable region thereof, it is possible to further enhance the positional accuracy of the affected portion.

Embodiment 3

Figure 3:
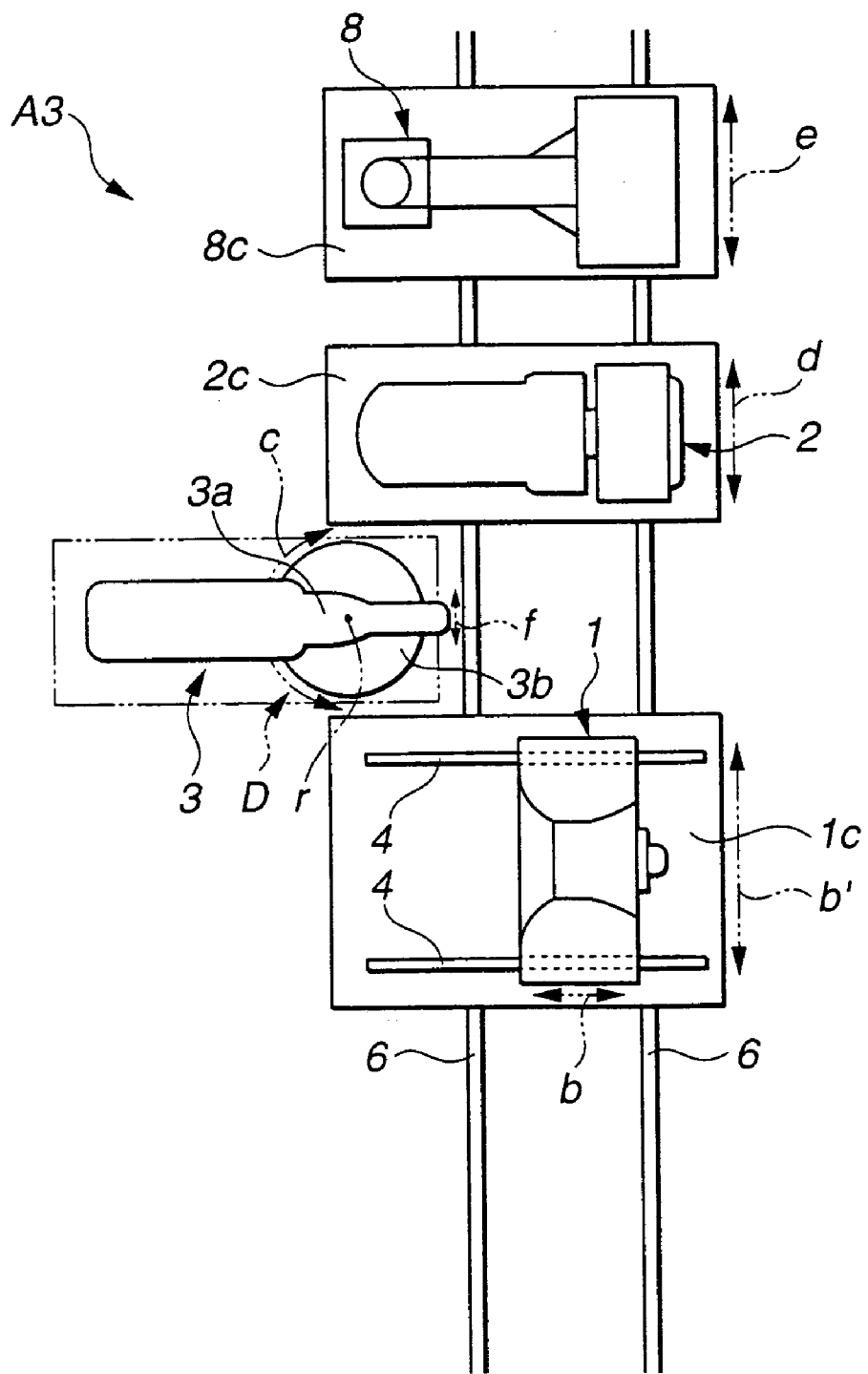
FIG. 3 is a schematic plan view of a third embodiment of the composite system for radiation therapy according to the present invention.

A composite system A3 for radiation therapy shown in FIG. 3 is modified from the composite system A2 such that the CT scanner 1 of the composite system A2 further includes a linear moving mechanism movable in the same direction as the moving direction of the irradiation apparatus 2. In the composite system A2 for radiation therapy shown in FIG. 2, the linear moving mechanism for moving the CT scanner 1 in the line direction (shown by the arrow "b") is mounted, together with the CT scanner, on a moving base 1c, and if the linear moving mechanisms for the irradiation apparatus 2 and the X-ray simulator 8 are of types using the rails 6, the rails 6 for the irradiation apparatus 2 are further extended, and the moving base 1c is configured as movable on the rails 6 in the same line direction (shown by an arrow "b'") as the moving direction of the irradiation apparatus 2 and the X-ray simulator 8, that is, in the y-axis direction (see FIG. 2) by control of a computer (not shown). Similarly, the irradiation apparatus 2 and the X-ray simulator 8 are mounted on moving bases 2c and 8c, respectively, and the moving bases 2c and 8c are configured as slidably movable on the rails. Even in this embodiment, each of these linear moving mechanisms is not limited to the mobile mechanism using the rails but may be configured as the above-described sliding mechanism for sliding each of the moving bases 1c, 2c, and 8c as the sliding floor. Also, even in this embodiment, the same common bed 3 as that used in the composite system A1 for radiation therapy may be used.

According to the composite system A3 for radiation therapy, in the case of positioning the common bed to a specific position of each apparatus, each apparatus to be used is moved in front of the common bed by the linear moving mechanism for the apparatus, and particularly, the CT scanner is further advanced to the common bed, whereby the common bed is located at the specific position at which the position of an affected portion of a patient can be checked by the CT scanner. If the common bed 3 has the isocentric rotation mechanism D, the isocentric rotation mechanism D can be used for each of the irradiation apparatus 2, CT scanner 1, and X-ray simulator 8. According to the present invention, like the composite system A1 for radiation therapy, the composite system A3 for radiation therapy may be configured not to be provided with the X-ray simulator 8.

Embodiment 4

Figure 4:
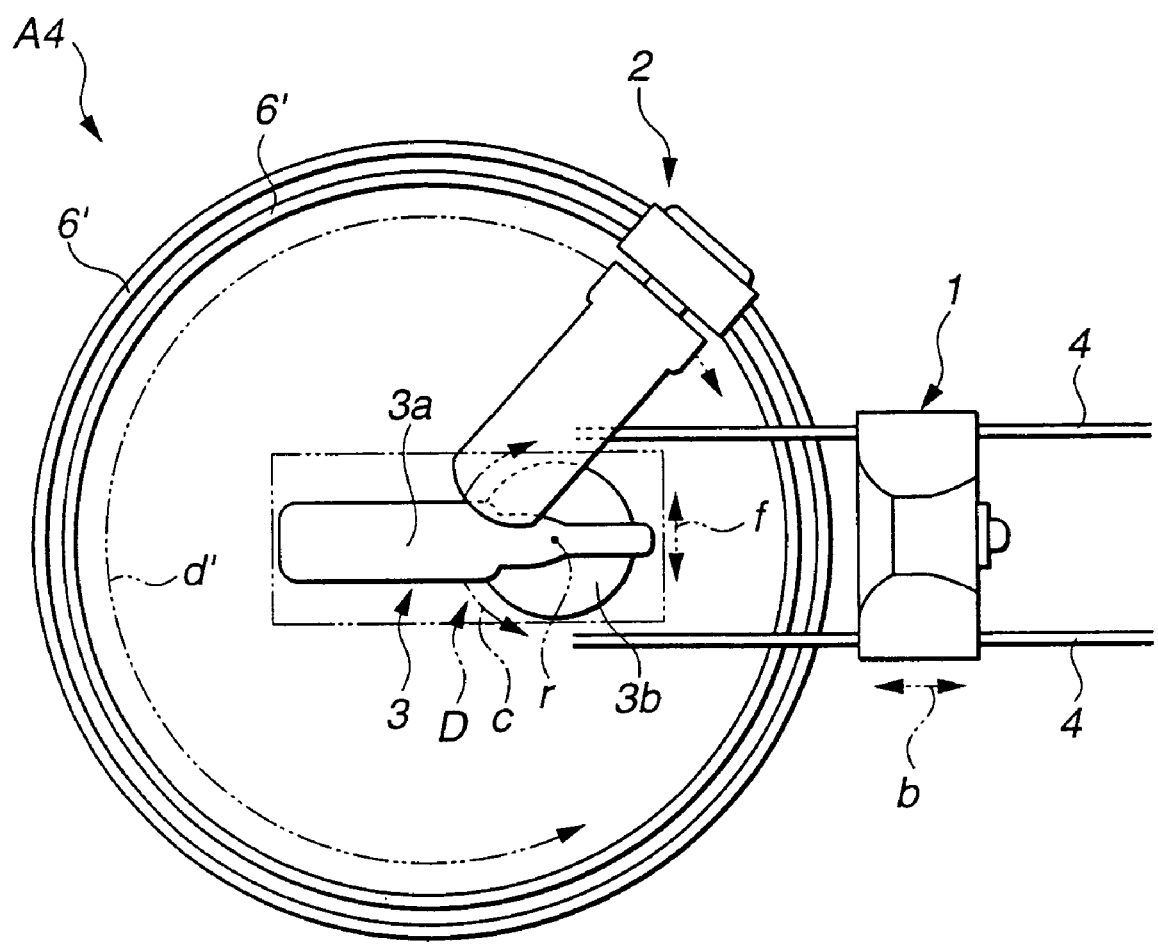
FIG. 4 is a schematic plan view of a fourth embodiment of the composite system for radiation therapy according to the present invention.

A fourth embodiment of the composite system for radiation therapy according to the present invention will be described with reference to FIG. 4. Referring to FIG. 4, there is shown a composite system A4 for radiation therapy according to this embodiment, which includes a CT scanner 1 including a linear moving mechanism movable to or from a common bed 3, and an irradiation apparatus 2 including a curvedly moving mechanism movable in the circumferential direction around the common bed 3. Here, according to the present invention, the curvedly moving mechanism for the irradiation apparatus may be movable in the circumferential direction centered at the common bed, as shown in the figure, or in the circumferential direction around the common bed which is positioned between the center of the movement circle of the irradiation apparatus and the circular-arc depicted by the curvedly moving mechanism, as shown in the FIG. 6. In other word, the position of the common bed 3 in the movement circle of the irradiation apparatus is not particularly limited, for example, the common bed may be positioned the center of the movement circle of the irradiation apparatus, or between the center of the movement circle and the circular-arc. In this embodiment, the curvedly moving mechanism is movable in the circumferential direction centered at the common bed 3, the moving direction of the CT scanner 1 crosses the moving direction of the irradiation apparatus 2, in other word, the moving range of the CT scanner crosses the moving range of the irradiation apparatus, and the common bed 3 used in this embodiment is positioned in the movement direction of the CT scanner 1 and also positioned at the center of the movement circle of the irradiation apparatus 2 and in the vicinity of a position (intersection) at which the moving directions of the CT scanner 1 and the moving direction of the irradiation apparatus 2 cross each other.

As described above, the moving mechanisms for each of the CT scanner 1 and the irradiation apparatus 2 of the composite system A4 for radiation therapy are not particularly limited but may be configured as follows. Examples of the moving mechanisms for the CT scanner 1 and the irradiation apparatus 2 include a mobile mechanism such as the above-described floor face mobile mechanism, the above-described ceiling mobile mechanism (not shown), or the above-described wall face mobile mechanism (not shown); and the above-described sliding mechanism. Examples of the linear moving mechanisms for the CT scanner 1 include the mobile mechanism which includes two CT scanner rails 4 installed on the floor face of the therapy room as described above, on the ceiling, or on wall face of wall bodies provided on both surfaces of the CT scanner 1, to allow the CT scanner 1 to be moved on the rails 4 in the line direction (shown by an arrow "b" in the figure) by control of a computer (not shown). Here, if the curvedly moving mechanism for the irradiation apparatus 2 is the floor face mobile mechanism type and the rails 6' are formed into circular shapes shown in the figure, the ceiling mobile mechanism type or the wall face mobile mechanism type may be used as the linear moving mechanism for the CT scanner 1 preferably.

Examples of the curvedly moving mechanisms for the irradiation apparatus 2 include the mobile mechanism which includes two rails 6' for the irradiation apparatus installed on the floor face of the therapy room, on the ceiling, or on wall face of wall bodies provided on both surfaces of the irradiation apparatus 2, in such a manner as to depict a circular-arc centered at the common bed 3, to allow the irradiation apparatus 2 to be moved on the rails 6' in the circumferential direction (shown by an arrow "d'"), that is, on the circular-arc depicted by the rails 6' by control of the computer (not shown). It is to be noted that the two rails 6' for the irradiation apparatus 2 may be replaced with only one rail.

Figure 5:
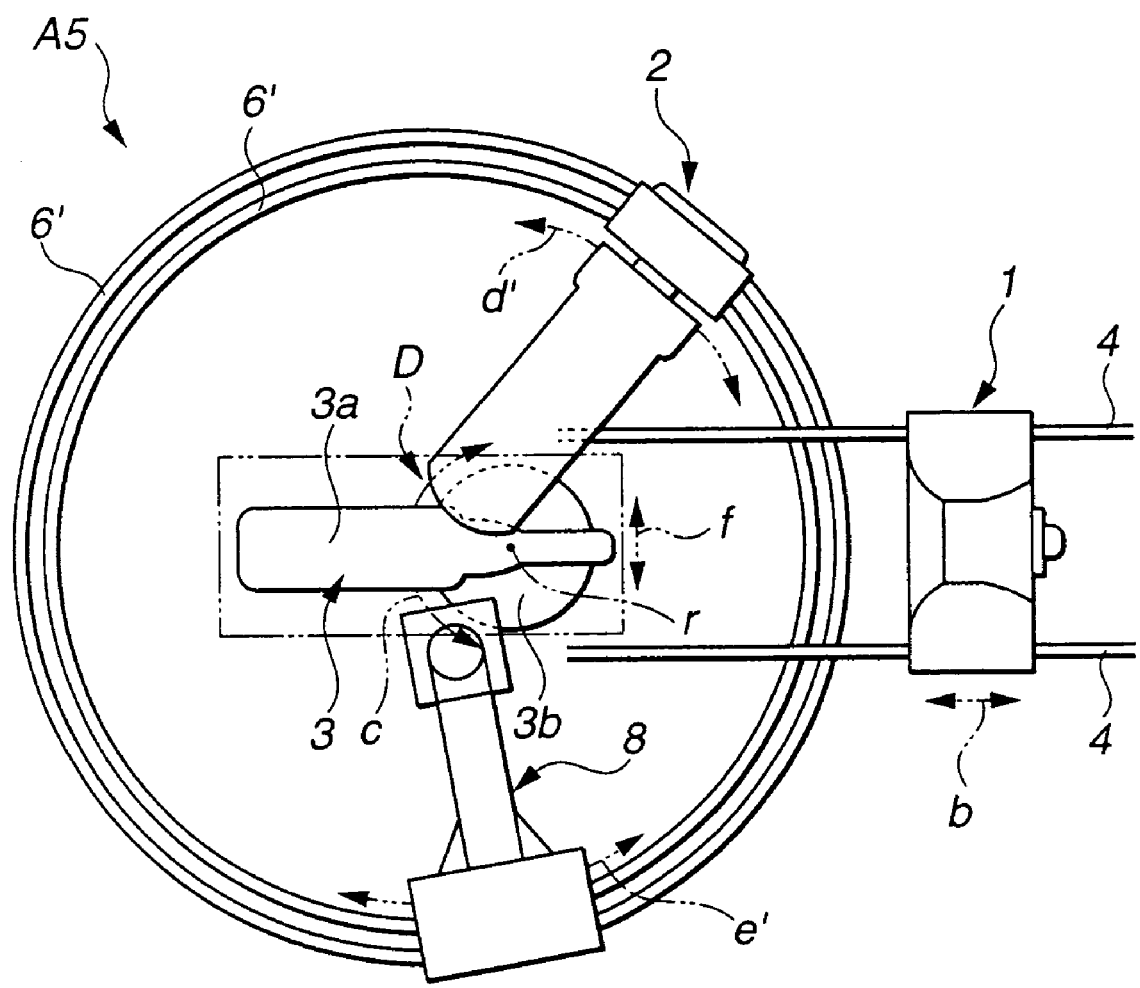
FIG. 5 is a schematic plan view of a fifth embodiment of the composite system for radiation therapy according to the present invention.

The rails 6' are not necessarily formed into circular shapes shown in the figure but may be formed into circular-arc shapes lacking rail portions located, for example, between the rails 4 for the CT scanner, or between the vicinity of the right side of the irradiation apparatus 2 in the figure and a position which is located across the rails 4 for the CT scanner in the clockwise direction, and which is equivalent to the leading end (on the counterclockwise side) of an arrow "d'" extending in the circumferential direction (the vicinity of the right side of the X-ray simulator 8 in FIG. 5). In addition, the common bed 3 is not necessary positioned at the center of the movement circle of the irradiation apparatus 2, for example, as described above, the common bed 3 may be positioned between the center of the movement circle of the irradiation apparatus 2 and the circular-arc depicted by the rails 6', as shown in the FIG. 6 and in the vicinity of the position to which the irradiation apparatus 2 is movable by the curvedly moving mechanism.

The common bed 3 used for the composite system A4 for radiation therapy may be represented by any therapy bed used for a general irradiation apparatus, more specifically, usable as the common bed for the composite system A1 for radiation therapy according to the first embodiment. In this composite system A4 for radiation therapy, radiation therapy can be performed without the need of movement of the common bed 3.

According to the composite system A4 for radiation therapy, a patient lies on the common bed 3, and the CT scanner 1 is linearly moved in the left direction in the figure, whereby the common bed 3 is located at the specific position of the CT scanner 1, to accurately confirm the position of an affected portion (lesion) of the patient lying on the common bed 3, and then the CT scanner 1 is linearly moved on the right direction in the figure, to be thus retracted. After that, the irradiation apparatus 2 is curvedly moved to the common bed 3 such that the affected portion of the patient is matched to an irradiation position in the circumferential direction along the circular-arc center at the common bed 3, to perform irradiation to the affected portion (lesion). In this way, according to the composite system A4 for radiation therapy in this embodiment, it is possible to reduce the degree of the movement of the bed between a position for alignment and a position for irradiation. In addition, if the CT scanner 1 in the composite system A4 for radiation therapy is configured as that used for the composite system A1 for radiation therapy, that is, configured so as to make the position of the affected portion of the patient adjustable in the lateral direction in the detectable region thereof, it is possible to further enhance the positional accuracy of the affected portion.

If the common bed 3 has the isocentric rotation mechanism D, it is possible to obtain the effect by the isocentric rotation mechanism D in each apparatus similarly to the composite system A1 for radiation therapy.

Embodiment 5

A composite system A5 for radiation therapy shown in FIG. 5 is modified from the composite system A4 for radiation therapy. If the curvedly moving mechanism of the irradiation apparatus 2 of the composite system A4 uses the rails 6', the composite system A5 is additionally provided with an X-ray simulator 8 including a mobile mechanism movable on the rails 6' in the same circumferential direction (shown by an arrow "e'") as the moving direction of the irradiation apparatus 2 by control of a computer (not shown). Even in this embodiment, the curvedly moving mechanism for the X-ray simulator 8 is not limited to the mobile mechanism using the rails but may be configured as the above-described sliding mechanism using the sliding floor. Also, even in this embodiment, the common bed as that in the composite system A1 for radiation therapy may be used. In addition, the configurations of the rails 4 and 6' are the same as those described in the composite system A4 for radiation therapy.

According to the composite system A5 for radiation therapy, in addition to the above-described function of the composite system A4 for radiation therapy, like the composite system A2 for radiation therapy, the above-described function and effect due to provision of the X-ray simulator 8 can be obtained by interrupting the irradiation, and shifting the irradiation apparatus 2 from the position of the common bed 3 and curvedly moving the X-ray simulator 8 to the common bed 3. Further, if the common bed 3 has the isocentric rotation mechanism D, the same function and effect due to provision of the isocentric rotation mechanism D as that described in the composite system A2 for radiation therapy can be obtained.

Embodiment 6

Figure 6:
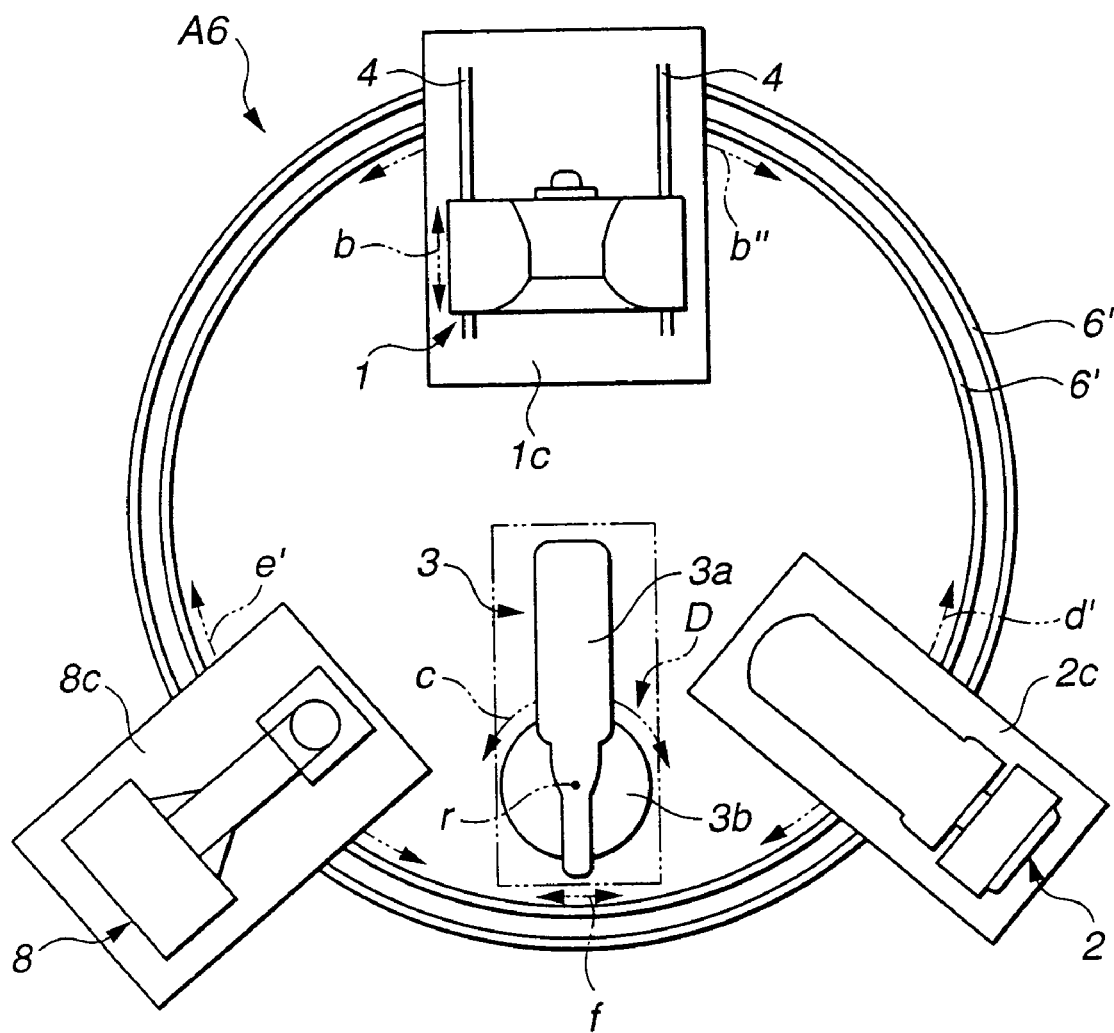
FIG. 6 is a schematic plan view of a sixth embodiment of the composite system for radiation therapy according to the present invention.

A composite system A6 for radiation therapy shown in FIG. 6 is modified from the composite system A5 for radiation therapy shown in FIG. 5 as follows: namely, the linear moving mechanism for moving the CT scanner 1 in the line direction (shown by the arrow "b") is mounted, together with the CT scanner 1, on a moving base 1c, and if the curvedly moving mechanisms for the irradiation apparatus 2 and the X-ray simulator 8 in the composite system A5 for radiation therapy are of types using the rails 6' extending in the circular shapes, the moving base 1c is configured such that the CT scanner 1 mounted on the moving base 1c is curvedly movable on the rails 6' in the same circumferential direction (shown by an arrow "b'"") as the moving direction of the irradiation apparatus 2 and the X-ray simulator 8 by control of a computer (not shown). Similarly, the irradiation apparatus 2 and the X-ray simulator 8 are mounted on moving bases 2c and 8c, respectively, and the moving bases 2c and 8c are configured as slidably movable on the rails.

In this embodiment, preferably, the rails 6' are formed into circular shapes. In addition, in this embodiment, the common bed 3 is positioned between the center of the movement circle of the apparatuses and the circular-arc depicted by the rails 6' shown in the figure, however, according to the present invention, the position of the common bed 3 in the circle is not particularly limited. For example, the common bed 3 may be positioned at the center of the movement circle, to be disposed in the vicinity a curve along which the apparatuses are movable, as shown in the FIG. 5. Also, even in this embodiment, each of these curvedly moving mechanisms is not limited to the mobile mechanism using the rails but may be configured as the above-described sliding mechanism for sliding each of the moving bases 1c, 2c, and 8c as the sliding floor. Further, even in this embodiment, the same common bed 3 as that used in the composite system A1 for radiation therapy may be used.

According to the composite system A6 for radiation therapy, in the case of positioning the common bed to a specific position of each apparatus, each apparatus to be used is moved in front of the common bed by the curvedly moving mechanism for the apparatus, and particularly, the CT scanner is further advanced to the common bed, whereby the common bed is located at the specific position. This is advantageous in enabling movement with a high positional accuracy, which is comparative to the movement in the composite system A5 for radiation therapy. If the common bed 3 has the isocentric rotation mechanism D, the isocentric rotation mechanism D can be used for each of the irradiation apparatus 2, CT scanner 1, and X-ray simulator 8. According to the present invention, like the composite system A3 for radiation therapy, the composite system A6 for radiation therapy may be configured not to be provided with the X-ray simulator 8.

Embodiment 7

Figure 7:
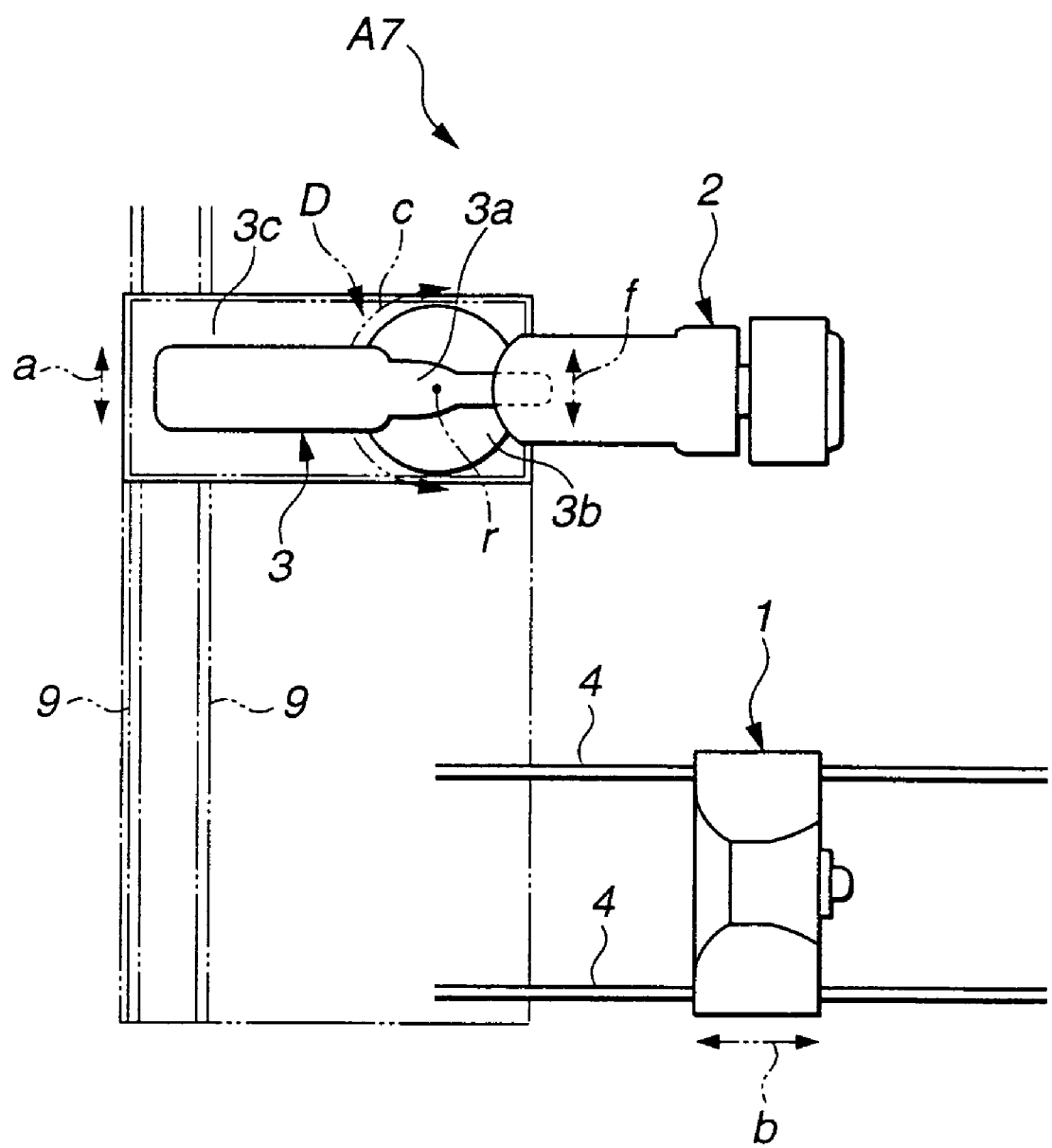
FIG. 7 is a schematic plan view of a seventh embodiment of the composite system for radiation therapy according to the present invention.

A seventh embodiment of the composite system for radiation therapy according to the present invention will be described with reference to FIG. 7. Referring to FIG. 7, there is shown a composite system A7 for radiation therapy, which includes a CT scanner 1 including a linear moving mechanism which is same as that used for the composite system A1 for radiation therapy and an irradiation apparatus 2 disposed in parallel to each other, and a common bed 3 including a linear moving mechanism for moving the common bed 3 in the direction cross the movement direction of the CT scanner 1, in particular, the linear moving mechanism for moving the common bed 3 in the direction perpendicular or substantially perpendicular to the movement direction of the CT scanner 1. The common bed 3 is configured as movable between a specific position of the CT scanner 1 and a specific position of the irradiation apparatus 2 on the basis of a command from a control unit (not shown).

The linear moving mechanism for the common bed 3 is not particularly limited. For example, the common bed becomes movable by any slidably movement mechanism such as the slide mechanism. In the examples shown in this figure, two rails 9 for moving the common bed 3 are installed on the floor face of the therapy room in such a manner as to make the common bed 3 movable (in such a manner as that the common bed 3 crosses) between the CT scanner 1 and the irradiation apparatus 2 disposed in parallel to each other, and the common bed 3 is slidably mounted to the rails 9 by mounting a moving base 3c, which is slidable on the rails 9 in the line direction (shown by an arrow "a" in the figure) by control of a computer (not shown), to the common bed 3, or the moving base 3c is configured as a sliding floor which is slidable in the line direction (shown by an arrow "a" in the figure) by control of a computer (not shown).

The common bed 3 may be configured as that including the isocentric rotation mechanism D, which is used in the composite system A1 for radiation therapy. In the case of using the common bed 3 of this type, it is preferred to mount the isocentric rotation mechanism D, together with the common bed 3, on the moving base 3c, for example, by installing the moving base 3c as the above-described floor face used for the isocentric rotation mechanism D and providing the turn table 3b on the moving base 3c. The linear moving mechanisms for the CT scanner 1 and the common bed 3 are preferably contrived such that the wall face or ceiling mobile mechanism is used as the moving mechanism for the CT scanner 1 in order to prevent interference between the moving base 3c and the moving mechanism for the CT scanner 1 at the time of movement of the common bed 3 to a position located in front of the CT scanner 1. In addition, the size and shape of the moving base 3c can be suitably selected.

Even in the composite system A7 for radiation therapy according to this embodiment, a patient usually lies on the common bed 3, and if the moving mechanism for the common bed 3 is controllable by the computer as described above, the common bed 3 can be accurately, linearly moved to a specific position on the basis of a command from the computer. To be more specific, at the time of alignment of an affected portion (lesion), the common bed 3 is linearly moved to a specific position of the CT scanner 1 and the CT scanner 1 is linearly moved to the common bed 3, to accurately check the position of the lesion of the patient, and at the time of irradiation to the affected portion, the CT scanner 1 is retracted from the common bed 3 and the common bed 3 is linearly moved to a specific position of the irradiation apparatus 2 on the basis of positional data given by the CT scanner 1, to perform irradiation to the lesion of the patient. With this configuration, it is possible to solve the related art problem associated with the rotational movement of a bed from alignment of an affected portion and radiation therapy for the affected portion, and hence to eliminate an error caused along with the rotational movement of the bed. In addition, if the CT scanner 1 in the composite system A7 in this embodiment is configured as that used for the composite system A1 for radiation therapy, that is, configured so as to make the position of the affected portion of the patient adjustable in the lateral direction in the detectable region thereof, it is possible to further enhance the positional accuracy of the affected portion. If the common bed 3 has the isocentric rotation mechanism D, it is possible to obtain the effect by the isocentric rotation mechanism D in each apparatus similarly to the composite system A1 for radiation therapy.

Embodiment 8

Figure 8:
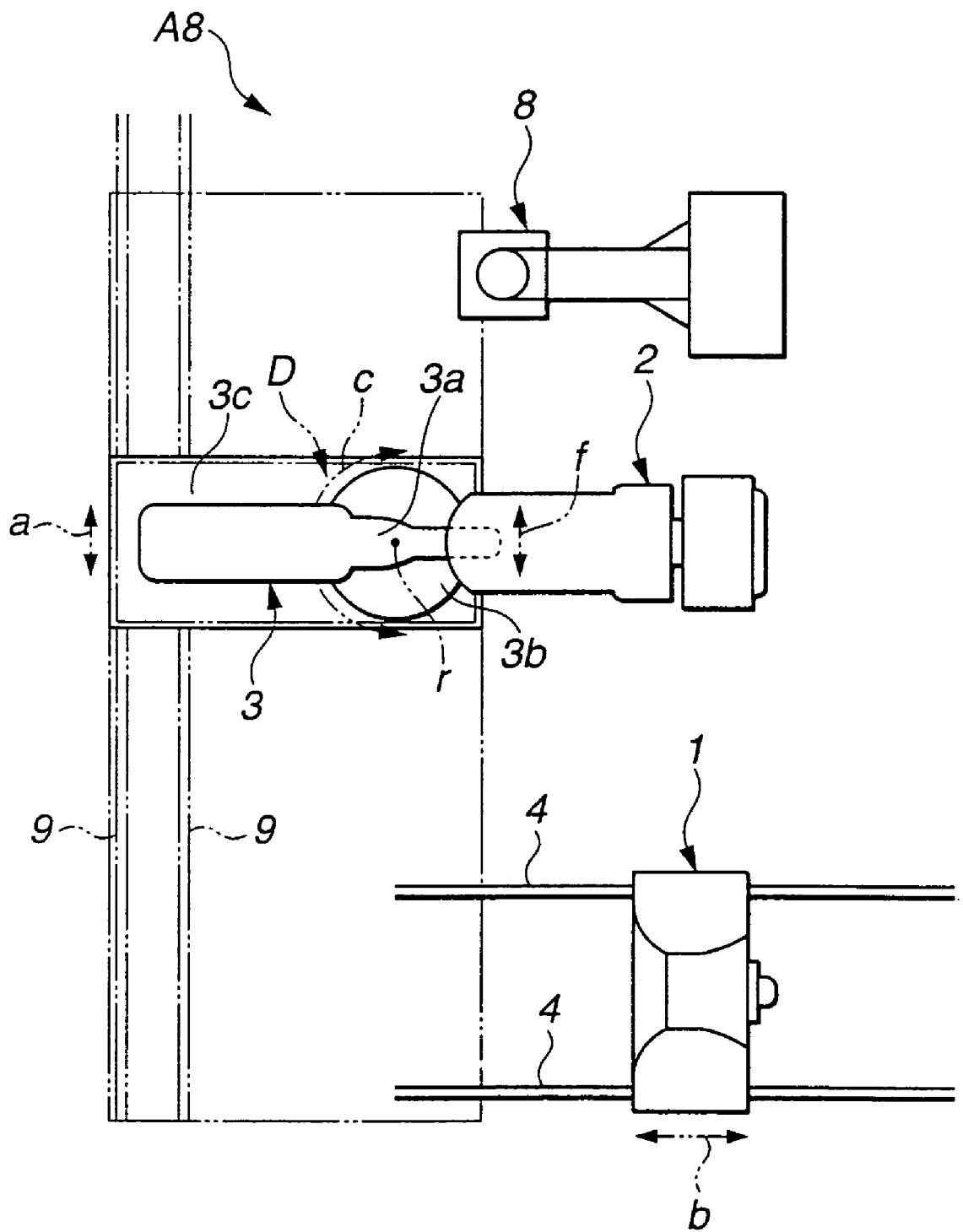
FIG. 8 is a schematic plan view of an eighth embodiment of the composite system for radiation therapy according to the present invention.

An eighth embodiment of the composite system for radiation therapy according to the present invention will be described with reference to FIG. 8. Referring to FIG. 8, there is shown a composite system A8 for radiation therapy according to the eighth embodiment. The composite system A8 for radiation therapy in this embodiment includes, in addition to the configuration of the composite system A7 for radiation therapy according to the seventh embodiment, an X-ray simulator 8. To be more specific, the lengths of the rails 9 for the common bed in the composite system A7 for radiation therapy are extended, or the slidable lengths of the moving base 3c in the composite system A7 for radiation therapy are extended, and the X-ray simulator 8 is provided so as to be in parallel to the irradiation apparatus 2. Even in the composite system A8 for radiation therapy according to this embodiment, in addition to the above-described function of the composite system A7 for radiation therapy, an additional function of checking a deviation in position of an affected portion of a patient can be obtained. To be more specific, by interrupting the irradiation, and linearly moving the common bed 3 in the upward direction in the figure to the specific position of the X-ray simulator 8, it can be checked, as described above, by the X-ray simulator 8 whether or not an affected portion of a patient is deviated from the aligned position. After the checking by the X-ray simulator 8, the common bed 3 may be returned to the original position. With this configuration, it is possible to re-start the irradiation to the affected portion in the state that the position of the affected portion has been accurately corrected.

If the common bed 3 has the isocentric rotation mechanism D, it is possible to use the isocentric rotation mechanism D for the X-ray simulator 8. Accordingly, it becomes possible to check more accurately whether or not an affected portion of a patient is deviated from the aligned position.

Embodiment 9 and Embodiment 10

Figure 9:
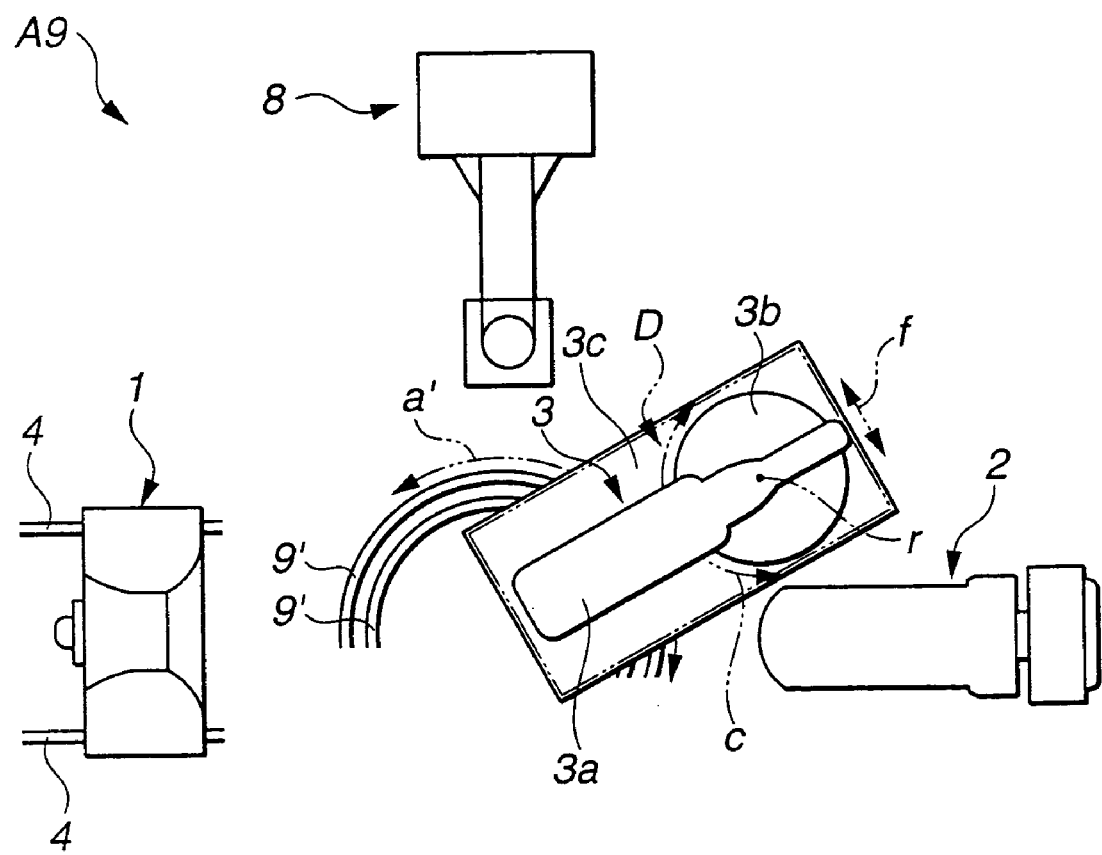
FIG. 9 is a schematic plan view of a ninth embodiment of the composite system for radiation therapy according to the present invention.
Figure 10:
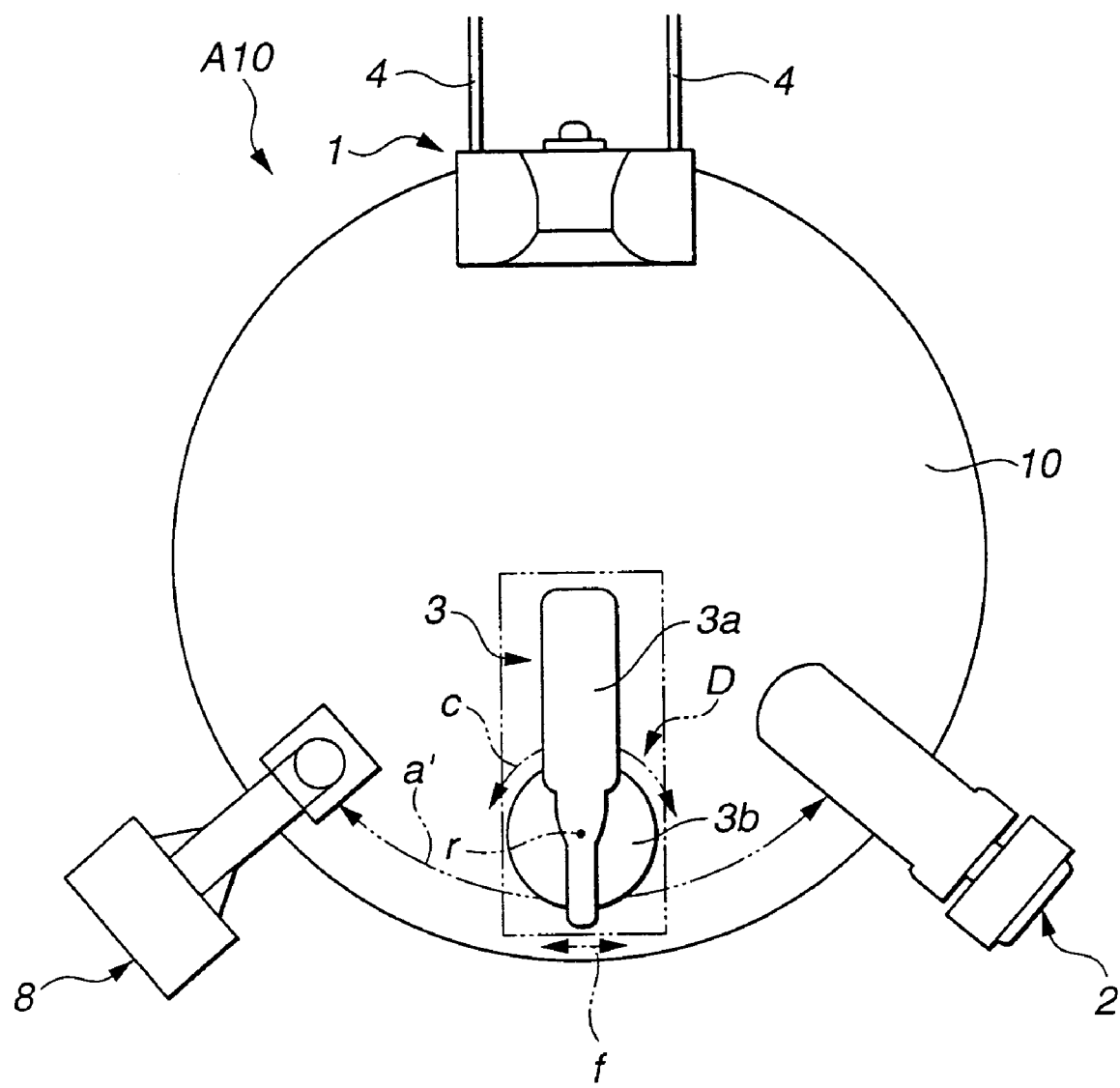
FIG. 10 is a schematic plan view of a tenth embodiment of the composite system for radiation therapy according to the present invention.

A composite system A9 for radiation therapy shown in FIG. 9 and a composite system A10 for radiation therapy shown in FIG. 10 are each configured such that a CT scanner 1 includes a linear moving mechanism movable along the longitudinal direction to the common bed 3 like the composite systems A7 and A8 for radiation therapy, and the CT scanner 1, an irradiation apparatus 2, and an X-ray simulator (optically used) are disposed in the vicinity of the curve along which a common bed 3 is movable, that is, at specific positions where the common bed 3 becomes usable by the curved movement of the common bed 3 to the front side of each apparatus. To be more specific, in the composite system A9 for radiation therapy shown in FIG. 9, the linear moving mechanism for the common bed 3 in the composite system A8 for radiation therapy shown in FIG. 8 is modified into a curvedly moving mechanism curvedly movable in the circumferential direction (shown by an arrow "a'"), for example, by using circular-arc shaped rails 9' in place of the linear rails 9 (see FIG. 8) of the linear moving mechanism. In the composite system A10 for radiation therapy shown in FIG. 10, the common bed 3 is configured as curvedly movable by mounting a circular turn table 10 on the floor face of the therapy room with its upper face set nearly at the same level as that of the upper plane of the floor face and mounting the moving base 3c on which the common bed 3 is mounted, together with the isocentric rotation mechanism D, on the turn table 10, or installing the turn table 10 as the above-described floor face used for the isocentric rotation mechanism, providing a turn table 3b for isocentric rotation, and mounting the common bed 3 on the turn table 10. According to the present invention, like the composite system A7 for radiation therapy, each of the composite systems A9 and A10 for radiation therapy may be configured not to be provided with the X-ray simulator 8.

The size of the turn table 10 (the position of the common bed 3 on the turn table 10) and the lengths and shapes of the curved rails 9' can be suitably selected depending on the size of each apparatus so as to prevent interference among the apparatuses. The arrangement of the apparatuses is not particularly limited. For example, the apparatuses may be disposed within a range of a circular-arc shape spread at about 180° as shown in FIG. 9, or disposed on the circumference at positions spaced at intervals of about 120° as shown in FIG. 10. In the case of the curvedly moving mechanism using the curved rails, such rails may be formed into circular shapes. Further, since it is desirable to make projections such as rails on the floor face of the therapy room as small as possible, the curved rails 9' of the composite system A9 for radiation therapy may be provided within the moving range of the common bed 3, and may be formed into semi-circular shapes or circular-arc shapes formed by cutting circular shapes into about ⅔ depending on the arrangement of the apparatuses.

Like the composite systems A7 and A8, each of the composite systems A9 and A10 for radiation therapy can move the common bed to a specific position by the curvedly moving mechanism without rotation on its axis, to thereby dispose the patient to be irradiated lying on the common bed at specific positions of the CT scanner 1, irradiation apparatus 2, and X-ray simulator 8 with a high positional accuracy. Also, if the common bed 3 has the isocentric rotation mechanism D, not only the irradiation apparatus 2 but also the CT scanner 1 and the X-ray simulator 8 can make use of the isocentric rotation mechanism D by moving the common bed 3 together with the isocentric rotation mechanism D provided on the common bed 3. Further, since the apparatuses of each of the composite systems A9 and A10 for radiation therapy are disposed in the vicinity of the curve along which the common bed is movable, the size of the entire composite system (arrangement dimension of each apparatus) can be made smaller than that in each of the composite systems A7 and A8 for radiation therapy.

In comparison of the curved motion of the common bed according to the present invention with the rotating motion of the above-described related art rotary type bed, the related art rotary type bed rotates on its axis, whereas the common bed according to the present invention curvedly revolves by making use of the rails or the turn table. For example, as the turn table of the composite system A10 for radiation therapy becomes small, the rotational axis of the turn table ultimately corresponds to the longitudinal center of the common bed 3, and in this case, the locus of the curved motion of the common bed corresponds to the locus of rotation of the related art rotary type bed. Even in this case, since the common bed does not rotate on its axis but curvedly by making use of the turn table, it is possible to significantly reduce the possibility of occurrence of offset of the coordinate due to rotation. In particular, if the common bed has the isocentric rotation mechanism, the isocentric rotation mechanism is moved along with the curved motion (revolution) of the common bed, not only the irradiation apparatus but also the CT scanner and the X-ray simulator can make use of the isocentric rotation mechanism. In addition, if the CT scanner 1 in each of the composite systems A9 and A10 for radiation therapy is configured as that used for the composite system A1 for radiation therapy, that is, configured so as to make the position of the affected portion of the patient adjustable in the lateral direction in the detectable region thereof, it is possible to further enhance the positional accuracy of the affected portion.

Embodiment 11

Figure 11:
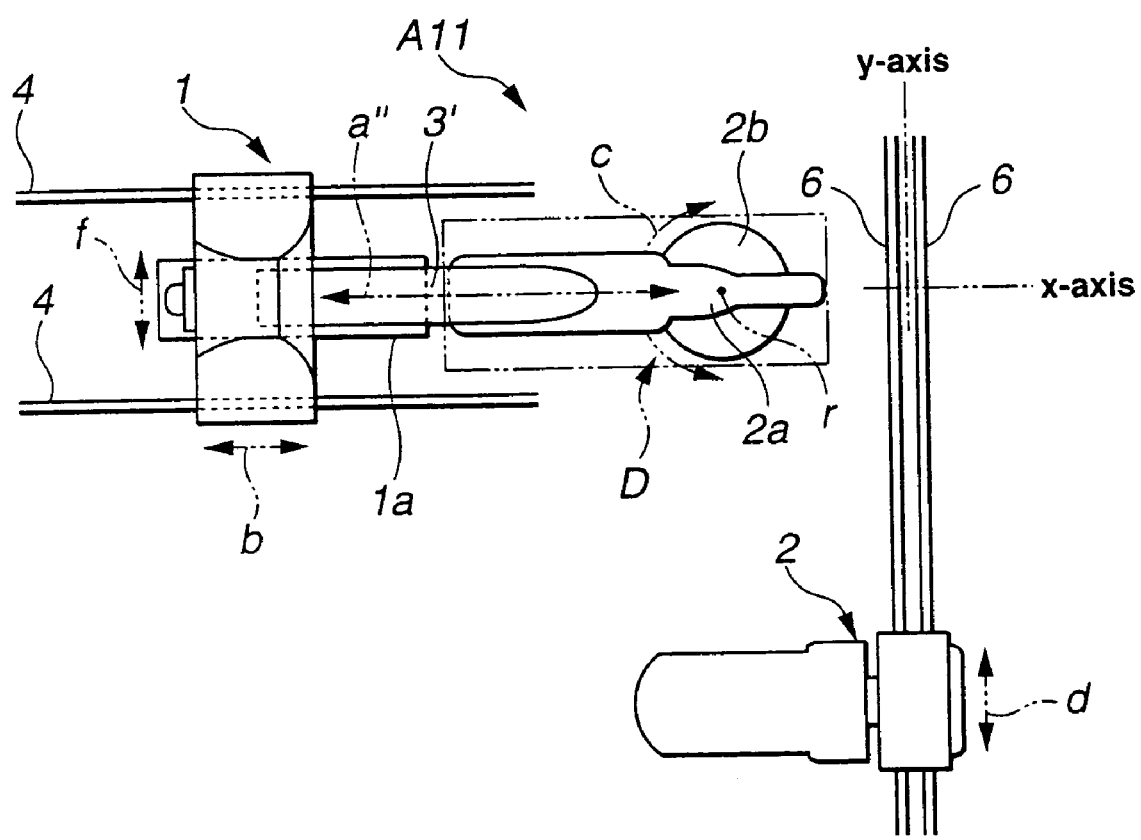
FIG. 11 is a schematic plan view of an eleventh embodiment of the composite system for radiation therapy according to the present invention.

An eleventh embodiment of the composite system for radiation therapy according to the present invention will be described with reference to FIG. 11. Referring to FIG. 11, there is shown a composite system A11 for radiation therapy according to the eleventh embodiment, which includes a CT scanner 1 having a linear moving mechanism and a irradiation apparatus 2 having a linear moving mechanism like the composite system A1 for radiation therapy, wherein the CT scanner 1 and the irradiation apparatus 2 are disposed in a therapy room in a state that the movement direction of the CT scanner 1 crosses the movement direction of the irradiation apparatus 2, in particular, the movement direction of the CT scanner 1 is perpendicular or substantially perpendicular to that of the irradiation apparatus 2, and disposed such that when these are arranged in parallel nearly along the x-axis direction in the figure by the movement of irradiation apparatus 2, they are oppose to each other. The CT scanner 1 uses a first bed 1a as a CT bed, and the irradiation apparatus 2 uses a second bed 2a as a therapy bed. The first bed 1a and the second bed 2a are disposed in series such that each bed 1a, 2a can be usable for the CT scanner 1, the irradiation apparatus 2. A common bed 3' is provided disposition of the common bed 3 that is used in common for all apparatus in the first composite system A1 for radiation therapy. The first bed 1a and the second bed 2a are connected to each other by means of a common bed 3' which is smoothly movable on the two beds 1a and 2a substantially in the x-axis direction in the figure. By such configuration, this composite system A11 for radiation therapy includes moving means that includes a moving mechanism for linearly moving the CT scanner 1 and the irradiation apparatus 2, and further includes a moving mechanism for linearly moving the common bed 3'. In addition, in this embodiment, the same linear moving mechanisms for linearly moving the CT scanner 1 and the irradiation apparatus 2 as that used in the composite system A1 for radiation therapy may be used preferably.

In this composite system A11 for radiation therapy, the diameter of the tunnel portion of the gantry of the CT scanner 1 is preferably as described above, and the CT scanner 1 preferably includes the positional adjustment means for adjusting the position of the patient in the lateral direction in the tunnel portion of the CT scanner 1. The positional adjustment means used for this composite system A11 for radiation therapy is not particularly limited but may be represented by any movement means (or adjustment means) known in the art. For example, the first bed (CT bed) 1a may be provided with a slide mechanism (not shown) for sliding the first bed (CT bed) 1a in the lateral direction (vertical direction in FIG. 11, shown by the arrow "f" in the figure) on the basis of preliminary scanning data of the CT scanner, or the first bed (CT bed) 1a may be provided with a slide mechanism (not shown) for sliding the common bed 3' placed on the first bed (CT bed) 1a in the lateral direction (vertical direction in FIG. 11, shown by the arrow "f" in the figure).

The second bed 2a as the therapy bed for the irradiation apparatus 2 may be represented by any therapy bed used for a general irradiation apparatus, which bed includes the isocentric rotation mechanism for adjustment in the circular direction (shown by an arrow "c" in the figure) to change the center of the irradiation field and the irradiation angle upon irradiation, and allows its positional adjustment in the longitudinal direction of the irradiation apparatus 2 and in the height direction, like as the common bed in the composite system A1 for radiation therapy.

The common bed 3' is configured to be smoothly movable in line on both the first bed 1a and the second bed 2a. The moving means for moving the common bed 3' is not particularly limited but may be represented by any linear moving mechanism known in the art. For example, the linear moving mechanism may include moving members such as (1) a roller, (2) a wheel, (3) a combination of moving rails provided on the upper surface of the first bed 1a and the upper surface of the second bed 2a, and a sliding portion provided on the back surface of the common bed 3' in such a manner as to be matched with the moving rails, and (4) a conveyor (belt conveyor). In this case, the driving units for driving the above-described moving members are exemplified by (1) a drive motor for rotating the roller, (2) a drive motor for rotating the wheel, (3) a drive source, connected to the common bed 3', for linearly moving the common bed 3' mounted on the moving rails by sliding motion of the sliding portion, and (4) a drive motor for operating the conveyor (belt conveyor).

In the case of using the roller as the moving member of the linear moving mechanism for linearly moving the common bed 3', for example, a plurality of rollers may be mounted on the upper surfaces of the first bed 1a and the second bed 2a in such a manner as to be spaced from each other at suitable intervals, and the common bed 3' is placed on these rollers. With this configuration, the common bed 3' on the rollers can be moved by rotating the rollers by means of the drive motor. In the case of using the wheel as the moving member, for example, a plurality of sets of wheels may be mounted on the common bed 3' in such a manner as to be spaced from each other at suitable intervals, and if needed, grooves forming a railway of the wheels are provided in the upper surfaces of the first bed 1a and the second bed 2a. With this configuration, the common bed 3' can be smoothly, linearly moved along the grooves functioning as the linear railway between the first bed 1a and the second bed 2a by driving the wheels by means of the drive motor. In the case of using the moving rails as the moving members, for example, in addition to moving rails on which the common bed 3' is to be placed, motion converting means for converting the rotation of the drive motor into lateral movement may be provided. With this configuration, the common bed 3' can be linearly moved by converting the rotation of the drive motor into lateral movement by means of the motion converting means. The motion converting means is exemplified by a combination of a ball screw extending from the first bed 1a to the second bed 2a and a nut fixed to the common bed 3'. In the case of using the conveyor as the moving member, for example, a belt conveyor may be provided on the upper surfaces of the first bed 1a and the second bed 2a, and the common bed 3' be placed on the conveyor. With this configuration, the common bed 3' can be moved by driving the conveyor by means of the drive motor.

The linear moving mechanism for linearly moving the common bed 3' according to this embodiment is preferably provided with a control unit for controlling the above-described drive unit by means of a computer. It is to be noted that the moving mechanism is not shown in the figure, and that the size and shape of the common bed 3' are not particularly limited insofar as the common bed 3' is movable between the first bed 1a and the second bed 2a in a state that a patient lies on the common bed 3'.

Additionally, the moving member of the linear moving mechanism for linearly moving the common bed 3' according to this embodiment may be operated manually, mechanically or automated.

According to the composite system A11 for radiation therapy in this embodiment, the patient to be irradiated lies on the common bed 3' placed on the upper surface of the first bed 1a, and the CT scanner 1 is linearly moved in the plus direction of the x-axis in the figure (the right direction in the figure), whereby the first bed 1a is located at the specific position of CT scanner 1, to accurately check the position of a lesion of the patient, and then the CT scanner 1 is linearly moved in the minus direction of the x-axis in the figure (the left direction in the figure) to be thus retracted. After that, the irradiation apparatus 2 is linearly moved to the second bed 2a such that the lesion of the patient is matched to an irradiation position in the plus direction of the y-axis in the figure (the upward direction in the figure) and the common bed 3' is linearly moved in the plus direction of the x-axis in the figure (the right direction in the figure) to move from the upper surface of the first bed 1a to the upper surface of the second bed 2a to perform irradiation to the lesion of the patient on the basis of the positional data checked by the CT scanner 1. In this way, according to the composite system A11 for radiation therapy in this embodiment, it is possible to reduce the degree of the linear movement of the bed between a position for alignment and a position for irradiation. In addition to the above-described advantage of this embodiment, if the CT scanner 1 is, as described above, configured to make the position of the affected portion of the patient to be irradiated adjustable (or movable) in the lateral direction in the detectable region. This makes it possible to enhance the accuracy of radiation therapy and facilitate the control of the accuracy thereof.

In addition, according to the composite system A11 for radiation therapy in this embodiment, the patient usually lies on the common bed 3', if the linear moving mechanism for the common bed 3' is controlled by a computer as described above, the common bed 3' can be accurately, linearly moved to a specific position on the basis of a command from the computer. This makes is possible that since the center of an affected portion (lesion) of a patient to be irradiated can be aligned to an actual origin in a three-dimensional space in the radiation therapy room.

Embodiment 12

Figure 12:
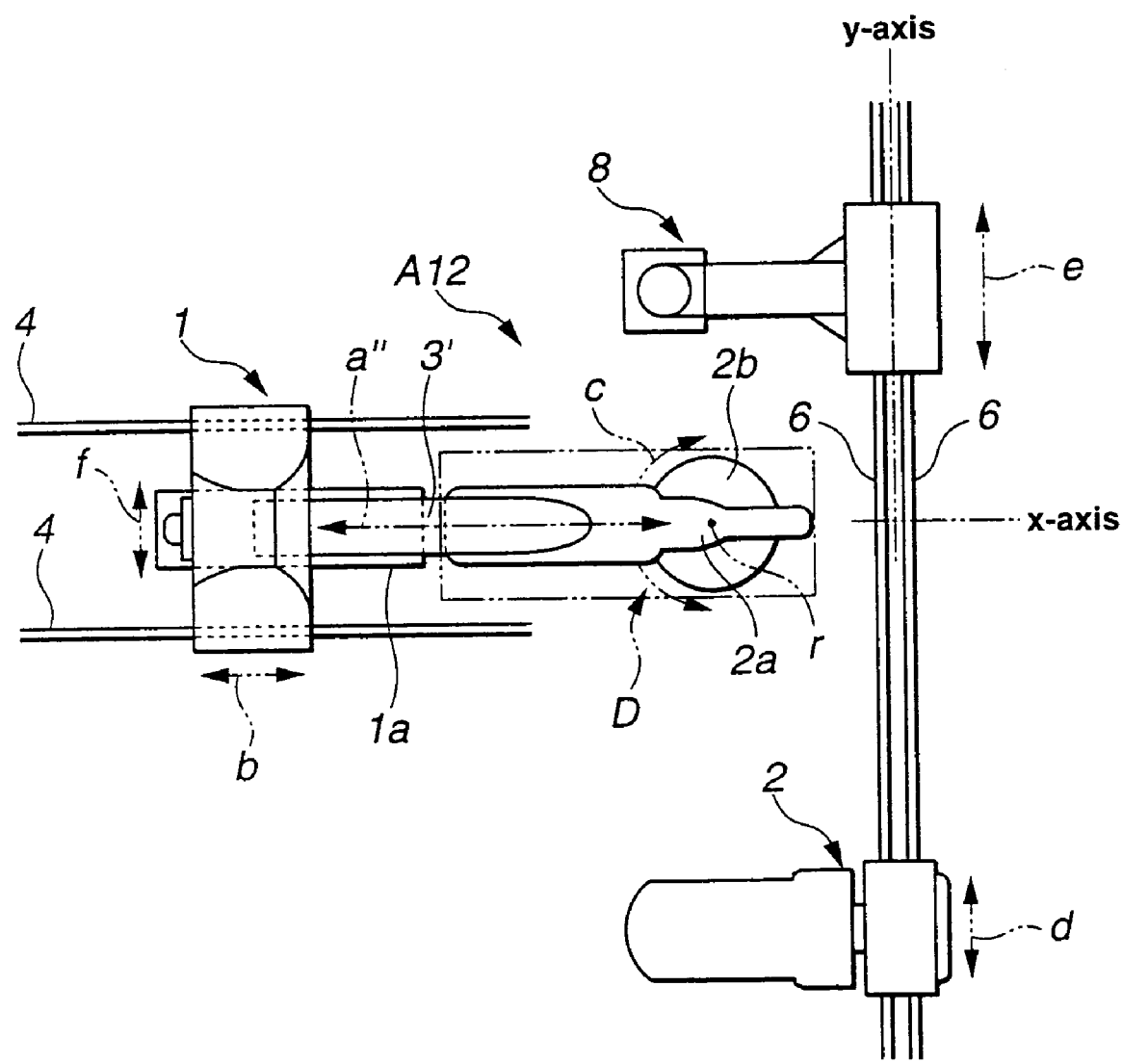
FIG. 12 is a schematic plan view of a twelfth embodiment of the composite system for radiation therapy according to the present invention.

A composite system A12 for radiation therapy shown in FIG. 12 is modified from the composite system A11 for radiation therapy such that an X-ray simulator including the linear moving mechanism (which is same as that used for the composite system A2 for radiation therapy) is added to the composite system A11 for radiation therapy as in the composite system A2 for radiation therapy. Like the composite system A11 for radiation therapy, a CT scanner 1 and an irradiation apparatus 2 are disposed such that when the CT scanner 1 and the irradiation apparatus 2 are arranged in parallel nearly along the x-axis direction in the figure by the movement of the irradiation apparatus 2, they are opposed to each other, and the X-ray simulator 8 is disposed such that when the CT scanner 1 and the X-ray simulator 8 are arranged in parallel nearly along the x-axis direction in the figure by the movement of the X-ray simulator 8, they are opposed to each other. Further, in place of the common bed 3 commonly used for all the apparatuses in the composite system A2 for radiation therapy, there are used the common bed 3', the first bed 1a, and the second bed 2a in the composite system A11 for radiation therapy, to allow not only linear movement of the CT scanner 1, the irradiation apparatus 2, and an X-ray simulator 8 but also linear movement of the common bed 3'.

According to the composite system A12 for radiation therapy, in addition to the above-described function of the composite system A11 for radiation therapy, an additional function of checking a deviation in position of an affected portion of a patient can be obtained. To be more specific, by interrupting the irradiation, shifting the irradiation apparatus 2 from the position of the second bed 2a that the common bed 3' is placed on the surface, and linearly moving the X-ray simulator 8 to the second bed 2a, it can be checked by the X-ray simulator 8 whether or not an affected portion of a patient is deviated from the aligned position by CT scanning due to the fact that the affected portion is moved in the body of the patient by, for example, the breath of the patient. After the checking by the X-ray simulator 8, both the irradiation apparatus 2 and the X-ray simulator 8 may be return to the original position by control of the computer (not shown). With this configuration, it is possible to re-start the irradiation to the affected portion in the state that the position of the affected portion has been accurately corrected. In addition, if the second bed 2a has the isocentric rotation mechanism D, it is possible to use the isocentric rotation mechanism D for the X-ray simulator 8.

Each of the above-described composite systems A1 to A12 for radiation therapy according to the first to the twelfth embodiments of the present invention exhibits the following effect: namely, at the time of radiation therapy for tumor or the like of a patient, the affected portion of the patient can be irradiated in a state that the position of the affected portion aligned by a CT scanner is accurately kept. As a result, it is possible to significantly enhance the control of the positional accuracy of the affected portion in radiation therapy and hence to significantly increase the effect of the radiation therapy.

Additionally, in above embodiments, the moving mechanisms for the CT scanner, the irradiation apparatus, the X-ray simulator and the common bed may be operated manually or mechanically, not only by the control of the computer. While the preferred embodiments have been described using the specific terms, such description is for illustrative purposes only, and it is to be understood that changes and variations may be made without departing from the spirit or scope of the following claims.

What is claimed is:

1. A composite system for radiation therapy, comprising:
    a CT scanner for checking the position of an affected portion of a patient to be irradiated;
    an irradiation apparatus for therapy, for disposing, on the basis of positional information of the affected portion checked by said CT scanner, the patient at a specific position at which the affected portion is aligned to an irradiation position, and performing irradiation to the affected portion;
    an X-ray simulator;
    a common bed used for said CT scanner, said irradiation apparatus and said X-ray simulator, in a state that the patient lies on said common bed, said bed including a positional adjustment means to allow the positional adjustment of a top plate of said common bed in a lateral direction, in a longitudinal direction and in a height direction;
    means for moving the patient from said CT scanner to the specific position of said irradiation apparatus and further moving the patient on said common bed to a specific position of said X-ray simulator;
    wherein said means for moving comprises a moving mechanism for linearly moving said CT scanner and said common bed; and
    said moving mechanism comprises a linear moving mechanism for said CT scanner, and a linear moving mechanism for said common bed, said linear moving mechanisms being disposed such that the movement directions of said CT scanner and said common bed cross each other,
    wherein said CT scanner is disposed in parallel to said irradiation apparatus, said irradiation apparatus is disposed in parallel to said X-ray simulator, and said common bed is linearly movable through its linear moving mechanism between said CT scanner, said irradiation apparatus and said X-ray simulator.

2. A composite system for radiation therapy according to claim 1, wherein said common bed comprises an isocentric rotation mechanism.

3. A composite system for radiation therapy according to claim 1, wherein a detectable region of said CT scanner has a diameter of a size to receive said common bed which is placed so that it is possible to adjust a position in the lateral direction in a detectable region of said CT scanner.

4. A composite system for radiation therapy according to claim 3:
    wherein said positional adjustment means adjusts the lateral position of the patient on said common bed in the detectable region of said CT scanner.

5. A composite system for radiation therapy according to claim 1, wherein said common bed is able to adjust a position within said CT scanner so that the affected portion is at a center point of said CT scanner.

6. A composite system for radiation therapy, comprising:
    a CT scanner for checking the position of an affected portion of a patient to be irradiated;
    an irradiation apparatus for therapy, for disposing, on the basis of positional information of the affected portion checked by said CT scanner, the patient at a specific position at which the affected portion is aligned to an irradiation position, and performing irradiation to the affected portion;

an X-ray simulator;

a common bed used for said CT scanner, said irradiation apparatus and said X-ray simulator, in a state that the patient lies on said common bed, said bed including a positional adjustment means to allow the positional adjustment of a top plate of said common bed in a lateral direction, in a longitudinal direction and in a height direction;

means for moving the patient from said CT scanner to the specific position of said irradiation apparatus and further moving the patient on said common bed to a specific position of said X-ray simulator;

wherein said means for moving comprises a moving mechanism for linearly moving said CT scanner and said common bed; and said moving mechanism comprises a linear moving mechanism for said CT scanner, and a linear moving mechanism for said common bed, said linear moving mechanisms being disposed such that the movement directions of said CT scanner and said common bed cross each other, wherein said CT scanner is disposed in parallel to said irradiation apparatus, said irradiation apparatus is disposed in parallel to said X-ray simulator, and said common bed is movable between said CT scanner, said irradiation apparatus and said X-ray simulator, wherein said linear moving mechanism for said common bed comprises a slide mechanism, including rails for said common bed so as to make said common bed movable between said CT scanner, said irradiation apparatus and said X-ray simulator and a moving base slidably mounted on said rails, said common bed being mounted on said moving base so as to be slidably mounted to said rails.

7. A composite system for radiation therapy according to claim 6, wherein said common bed comprises an isocentric rotation mechanism mounted on said moving base.

* * * * *